US010240042B2

(12) United States Patent
Kuks et al.

(10) Patent No.: US 10,240,042 B2
(45) Date of Patent: *Mar. 26, 2019

(54) PHOTOLUMINESCENT COMPOUNDS AND USES THEREOF

(71) Applicant: StoreDot Ltd., Herzeliya (IL)

(72) Inventors: Evgenia Liel (Jeny) Kuks, Ramat Gan (IL); Rony Schwarz, Kibbutz Ma'anit (IL); Eran Sella, Tel-Aviv (IL); Mor Shmuel Armon, Ramat Gan (IL); Daniel Szwarcman, Pardes-Hanna Karkur (IL)

(73) Assignee: StoreDot Ltd., Herzeliya (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/661,151

(22) Filed: Jul. 27, 2017

(65) Prior Publication Data

US 2018/0057689 A1 Mar. 1, 2018

Related U.S. Application Data

(63) Continuation of application No. 15/252,597, filed on Aug. 31, 2016, now Pat. No. 10,100,197.

(51) Int. Cl.
| | | |
|---|---|---|
| *C09B 11/24* | (2006.01) | |
| *F21V 9/30* | (2018.01) | |
| *C09K 11/06* | (2006.01) | |
| *C07D 311/82* | (2006.01) | |
| *G02F 1/1335* | (2006.01) | |

(52) U.S. Cl.
CPC ............ *C09B 11/24* (2013.01); *C07D 311/82* (2013.01); *C09K 11/06* (2013.01); *F21V 9/30* (2018.02); *G02F 1/133617* (2013.01); *C09K 2211/1022* (2013.01); *C09K 2211/1088* (2013.01); *G02F 2001/133614* (2013.01)

(58) Field of Classification Search
CPC ......... C09B 11/24; C07D 311/82; F21V 9/30; G02F 1/133617; G02F 2001/133614; C09K 11/06; C09K 2211/1022; C09K 2211/1088
See application file for complete search history.

(56) References Cited

U.S. PATENT DOCUMENTS

| | | | |
|---|---|---|---|
| 3,996,192 | A | 12/1976 | Hahnke et al. |
| 5,250,214 | A | 10/1993 | Kanemoto et al. |
| 5,459,268 | A | 10/1995 | Haugland et al. |
| 5,686,261 | A | 11/1997 | Zhang et al. |
| 5,851,621 | A | 12/1998 | Wolleb et al. |
| 7,704,284 | B2 | 4/2010 | Eliu et al. |
| 8,163,910 | B2 | 4/2012 | Lukhtanov |
| 8,580,579 | B2 | 11/2013 | Hell et al. |
| 8,735,444 | B2 | 5/2014 | Hell et al. |
| 9,771,480 | B2 | 9/2017 | Kuks et al. |
| 9,868,859 | B2 | 1/2018 | Szwarcman et al. |
| 2004/0135502 | A1 | 7/2004 | Kobayashi et al. |
| 2004/0142137 | A1 | 7/2004 | Lehmann et al. |
| 2004/0225037 | A1 | 11/2004 | Lam et al. |
| 2005/0170363 | A1 | 8/2005 | Reddington et al. |
| 2007/0134596 | A1 | 6/2007 | Lungu |
| 2009/0004462 | A1 | 1/2009 | Zhang et al. |
| 2009/0213296 | A1 | 8/2009 | Park et al. |
| 2009/0306277 | A1 | 12/2009 | Goenner et al. |
| 2010/0183805 | A1 | 7/2010 | Nieminen |
| 2010/0330380 | A1 | 12/2010 | Colreavy et al. |
| 2011/0082273 | A1 | 4/2011 | Laas et al. |
| 2012/0024345 | A1 | 2/2012 | Reisfeld et al. |
| 2012/0135459 | A1 | 5/2012 | Hell et al. |
| 2012/0138124 | A1 | 6/2012 | Shmueli et al. |
| 2014/0118814 | A1* | 5/2014 | Uhm ...................... G02F 1/157 359/273 |
| 2014/0186679 | A1 | 7/2014 | Archer et al. |
| 2014/0208978 | A1 | 7/2014 | Sunder et al. |
| 2016/0146987 | A1 | 5/2016 | Ito et al. |
| 2016/0251516 | A1 | 9/2016 | Sorensen et al. |
| 2017/0037259 | A1 | 2/2017 | Wang |
| 2017/0137626 | A1 | 5/2017 | Kuks et al. |
| 2017/0137627 | A1 | 5/2017 | Szwarcman et al. |
| 2017/0137628 | A1 | 5/2017 | Szwarcman et al. |
| 2017/0137630 | A1 | 5/2017 | Szwarcman et al. |
| 2017/0137705 | A1 | 5/2017 | Szwarcman et al. |
| 2017/0139270 | A1 | 5/2017 | Szwarcman et al. |
| 2017/0139271 | A1 | 5/2017 | Szwarcman et al. |
| 2017/0139277 | A1 | 5/2017 | Szwarcman et al. |
| 2017/0283616 | A1 | 10/2017 | Kuks et al. |
| 2018/0051174 | A1 | 2/2018 | Szwarcman et al. |

(Continued)

FOREIGN PATENT DOCUMENTS

| | | |
|---|---|---|
| EP | 0805441 | 11/1997 |
| EP | 2253635 | 11/2010 |
| EP | 2305691 | 4/2011 |

(Continued)

OTHER PUBLICATIONS

Madsen et al. "Synthesis of Rhodamine 6G-Based Compounds for the ATRP Biocompatible polymers", Biomacromolecules, Jun. 13, 2011, vol. 12, No. 6, pp. 2225-2234.
International Search Report of PCT Application No. PCT/IL2016/050955 dated Nov. 23, 2016.
Drexhage, K. H. "Fluorescence efficiency of laser dyes. [Xanthenes, oxazines 7-aminocoumarins]" J. Res. Natl. Bur. Stand., A; 1976 vol. 80:3.
Mitronova et al. "New fluorinated rhodamines for optical microscopy and nanoscopy", Chemistry. Apr. 19, 2010;16(15):4477-88.
Mottram et al. "Hydrophobic analogues of rhodamine B and rhodamine 101: potent fluorescent probes of mitochondria in living C. elegans", Beilstein J Org Chem. 2012;8:2156-65.

(Continued)

*Primary Examiner* — John M Mauro
(74) *Attorney, Agent, or Firm* — Pearl Cohen Zedek Latzer Baratz LLP

(57) ABSTRACT

This invention is directed to photoluminescent compounds based on rhodamine dyes with green emission and uses thereof for photoluminescence based devices.

8 Claims, 7 Drawing Sheets

(56) References Cited

U.S. PATENT DOCUMENTS

2018/0105696 A1     4/2018   Kuks et al.

FOREIGN PATENT DOCUMENTS

| EP | 2752464 | 7/2014 | |
|---|---|---|---|
| JP | 62278570 | 12/1987 | |
| JP | 2005/002290 | 1/2005 | |
| JP | 2006/306933 | 11/2006 | |
| JP | 2012/233151 | 11/2012 | |
| WO | WO-2004/101709 | 11/2004 | |
| WO | WO 2010/149190 A1 | 12/2010 | |
| WO | WO-2011/123820 | 10/2011 | |
| WO | WO-2013/056720 | 4/2013 | |
| WO | WO-2013103156 A1 * | 7/2013 | ......... G01N 33/5073 |
| WO | WO-2015/016175 | 2/2015 | |
| WO | WO 2016/121194 | 8/2016 | |
| WO | WO-2017/085720 | 5/2017 | |

OTHER PUBLICATIONS

Sinel'Nikov et al. "Fluorescence of the lactone form of rhodamine B", Russian Journal of Physical Chemistry A Aug. 2013, vol. 87, Issue 8, pp. 1409-1416.
Zhang et al. "Fluorescence lifetimes and quantum yields of ten rhodamine derivatives: Structural effect on emission mechanism in different solvents", Journal of Luminescence vol. 145, Jan. 2014, pp. 448-453.
U.S. Appl. No. 15/252,597, filed Aug. 31, 2016, Kuks et al.
U.S. Appl. No. 15/691,774, filed Aug. 31, 2017, Armon et al.
U.S. Appl. No. 15/691,775, filed Aug. 31, 2017, Szwarcman et al.
U.S. Appl. No. 15/691,776, filed Aug. 31, 2017, Kuks et al.
International Search Report for PCT application No. PCT/IL2016/051234, dated Mar. 14, 2017.
Reisfeld, Reneta. Doped polymeric systems produced by sol-gel technology: optical properties and potential indusrial applications. Polimery-Warsaw, 2006, 51.2: 95. Dec. 1, 2006.
Inoue et al. "Development of Color Resists Containing Novel Dyes for Liquid Crystal Displays" translated from R&D Report, "Sumitomo Kagaku", Nov. 35, 2013, pp. 1-7.
Uddin et al. "Synthesis of 5- and 6-Carboxy-X-rhodamines", Organic Letters, Nov. 6, 2008, vol. 10, No. 21, pp. 4799-4801.
Soibinet et al. "Rhod-5N as a fluorescent molecular sensor of cadmium(II) ion", J Fluoresc. Nov. 2008;18(6):1077-82.
Pal et al. "Spectroscopic and photophysical properties of some new rhodamine derivatives in cationic, anionic and neutral micelles", Journal of Photochemistry and Photobiology A: Chemistry vol. 98, Issues 1-2, Aug. 2, 1996, pp. 65-72.
Ross et al. "Facile Synthesis of Rhodamine Esters using Acetyl Chloride in Alcohol Solution", Journal Synthetic Communications vol. 36, 2006—Issue 12, p. 1745-1750.
Belov et al. "Rhodamine spiroamides for multicolor single-molecule switching fluorescent nanoscopy", Chemistry. Oct. 19, 2009;15(41):10762-76.
Lakowicz, "Principles of Fluorescence Spectroscopy", Springer, third edition, 2006.
Kobayashi et al. "LCD Backlights", Wiley, 2009.
Kim et al. "Sol—Gel Derived Transparent Zirconium-Phenyl Siloxane Hybrid for Robust High Refractive Index LED Encapsulant";ACS Applied Materials & Interfaces, Feb. 24, 2014, vol. 6, No. 5, pp. 3115-3121.
Reisfeld et al. "Solid-state lasers based on inorganic-organic hybrid materials obtained by combined sol-gel polymer technology", Polym. Adv. Technol., May 19, 2004, vol. 15, No. 6, pp. 291-301.
Kazes et al. "Organic-Inorganic Sol-Gel Composites Incorporating Semiconductor Nanocrystals for Optical Gain Applications", Advanced Materials, May 4, 2009, vol. 21, No. 17, pp. 1716-1720.
Kazes et al. "Blue laser dye spectroscopic properties in solgel inorganic-organic hybrid films", Optics Letters, Feb. 1, 2006, vol. 31, No. 3, pp. 356-358.

Deshpande et al. "Efficient lasing acting from Rhodamine-110 (RH-110) impregnated sol-gel silica samples prepared by dip method", Journal of Luminescence, May 2010, vol. 130, No. 5, pp. 839-844.
Yariv et al. "Efficiency and photostabilty of dye-doped solid-state lasers in different hosts" Optical Materials, Feb. 2001, vol. 16. No. 1-2, pp. 29-38.
Geffroy et al. "Organic light-emitting diode (OLED) technology: materials, devices and display technologies", Polymer International, 2006, vol. 55, pp. 572-582.
Liu et al. "Manipulation of exciton distribution for high-performance fluorescent/phosphorescent hybrid white organic light-emitting diodes", Journal of Materials Chemistry C, 2017, vol. 5, pp. 7668-7683.
Reineke et al. "White organic light-emitting diodes: Status and perspective", Reviews of Modern Physics, Jul. 30, 2013, vol. 85, No. 3, pp. 1245-1293.
Nguyen et al., "Practical Synthetic Route to Functionalized Rhodamine Dyes", Organic Letters, Sep. 1, 2003, vol. 5, No. 18, pp. 3245-3248.
Kolmakov et al. "Polar Red-Emitting Rhodamine Dyes with Reactive Groups: Synthesis, Photophysical Properies, and Two-Color STED Nanoscopy Applications", Chemistry—A European Journal, Dec. 11, 2013, vol. 20, No. 1, pp. 146-157.
Gyuzel et al. "Functionalization of the meso-phenyl Ring of Rhodamine Dyes Trough S N Ar with Sulfur Nuclephiles: Synthesis, Biophysical Characterization, and Comprehensive NMR Analysis", European Journal of Organic Chemistry, Jan. 1, 2015 vol. 2015, No. 2, pp. 337-349.
Polyakova et al. "New GM1 Ganglioside Derivatives for Selective Single and Double Labelling of the Natural Glycosphingolipid Skeleton", Eur. J. Org. Chem., 2009, pp. 5162-5177.
Rhodamine Dyes, IUPAC Gold Book, 1995, accessed Aug. 7, 2017.
Jbeily et al. "Synthesis of fluorinated rhodamines and application for confocal laser scanning microscopy", Journal of Fluorine Chemistry, 2016, pp. 70-78.
U.S. Office Action for U.S. Appl. No. 15/622,158, dated Jan. 26, 2018.
U.S. Office Action for U.S. Appl. No. 15/691,776, dated Feb. 14, 2018.
Peter Edman et al."Extended Förster theory of donor—donor energy migration in bifluorophoric macromolecules. Part II. Method for determining intramolecular distances with experimental validation using mono and bifluorophoric systems" Physical Chemistry Chemical Physics, pp. 2795-2801, May 25, 2000.
SciFinder 2018, American Chemical Society (ACS) Registry Excerpts, 24 pages.
Chemical Abstracts Service 2018 American Chemical Society Registry Excerpts p. 1.
U.S. Final Office Action for U.S. Appl. No. 15/622,158, dated Mar. 27, 2018.
U.S. Notice of Allowance for U.S. Appl. No. 15/691,774, dated Apr. 3, 2018.
U.S. Appl. No. 15/924,302, filed Mar. 19, 2018, Szwarcman et al.
U.S. Appl. No. 15/959,329, filed Apr. 23, 2018, Szwarcman et al.
U.S. Office Action for U.S. Appl. No. 15/785,443, dated May 3, 2018.
U.S. Appl. No. 16/005,730, filed Jun. 12, 2018, Schwarz et al.
Office Action for U.S. Appl. No. 15/841,347, dated Dec. 27, 2018.
Young-Hoon Ahn et al. "Combinatorial Rosamine Library and Application to in Vivo Glutathione Probe" *J. Am. Chem. Soc.*, Mar. 23, 2007 , 129 (15), pp. 4510-4511.
Young-Hoon Ahn et al. "Combinatorial Rosamine Library and Application to in Vivo Glutathione Probe" *J. Am. Chem. Soc.*, Mar. 23, 2007, 129 (15), Supporting Information pp. S1-S15.
Siang Hui Lim, et al. "Rosamines Targeting the Cancer Oxidative Phosphorylation Pathway" PLoS One. Mar. 12, 2014; 9(3): e82934.
Database Registry Chemical Abstracts Service, Columbus Ohio, accesses via SCIFINDER, Dec. 18, 2018, pp. 1-2.

\* cited by examiner

PHOTOLUMINESCENT COMPOUNDS AND USES THEREOF

CROSS-REFERENCE TO RELATED APPLICATIONS

This application is a continuation of U.S. application Ser. No. 15/252,597, filed Aug. 31, 2016, which is incorporated by reference in its entirety.

FIELD OF THE INVENTION

This invention is directed to photoluminescent compounds based on rhodamine dyes with green emission and uses thereof for photoluminescence based devices.

BACKGROUND OF THE INVENTION

Xanthene derived dyes are known to be efficient fluorescent dyes. Generally speaking, functional groups on the conjugated moiety of the dye (chromophore) have the ability to fine tune the dye's fluorescent colors and so is the case with, more specifically, xanthenes. For instance, fluorescein is a green emitting fluorescent compound that has an emission peak at 515 nm, whereas the anionic dye of eosin that can be regarded as the brominated fluorescein, emits at 544 nm—a significant bathochromic shift.

Some xanthene derived dyes consist of the Rhodamine dyes. These compounds can be regarded as diaminated analogs of xanthene (at the positions 6' and 3'; see below for further elaboration on the numbering convention of rhodamine) which has been additionally arylated at the 9' position. Rhodamines fluoresce and have been used extensively in research, both as free dye and as conjugates to larger molecules, e.g. proteins and antibodies as biomarkers.

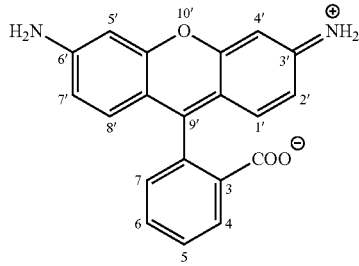

Rhodamines are outstanding versatile organic dyes. They demonstrate thermal and photochemical stability, strongly absorb visible light, and show high fluorescence quantum yields. Rhodamine based compounds have been utilized as industrial dyes, electronic materials, medical devices, bio markers, lighting devices, sensors and photovoltaics. Within the rhodamine family of compounds, one of the commonly used fluorescent rhodamine dye is rhodamine 6G which has high quantum yield and high photostability, rendering it a suitable compound in optical and electro optical applications, as well as biotechnological applications. This example of rhodamine 6G along with other ones such as, for example sulforhodamine 101 and rhodamine 101 show that there is a significant need in the dyes and pigments industry for the synthesis of new fluorescent dyes with superior optical and electro optical parameters such as fluorescence intensity, quantum yield and photostability. Said synthetic compounds form the basis of numerous novel (bio)optical and (bio)electro-optical devices.

SUMMARY OF THE INVENTION

In one embodiment, this invention is directed to a photoluminescent compound represented by the structure of formula (I):

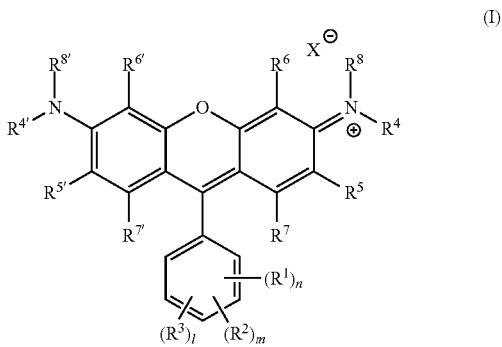

wherein $R^1$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

$R^2$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

$R^3$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

$R^4$, $R^{4'}$, $R^8$ and $R^{8'}$ are each independently selected from H, alkyl, haloalkyl, heterocycloalkyl, cycloalkyl, aryl and benzyl;

$R^5$ and $R^{5'}$ are each independently selected from Z, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide;

$R^6$, $R^{6'}$, $R^7$ and $R^{7'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide; or $R^4$ and $R^5$ or $R^{4'}$ and $R^{5'}$ form together a N-heterocyclic ring wherein said ring is optionally substituted;

$Q^1$ and $Q^2$ are each independently selected from H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —OC(O)N(H)$Q^4$, —OC(S)N(H)$Q^4$, —N(H)C(O)N($Q^3)_2$ and —N(H)C(S)N($Q^3)_2$;

Z is selected from alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —OC(O)N(H)$Q^4$, —OC(S)N(H)$Q^4$, —N(H)C(O)N($Q^3)_2$ and —N(H)C(S)N($Q^3)_2$;

$Q^3$ and $Q^4$ are each independently selected from H, alkyl, haloalkyl, heterocycloalkyl, cycloalkyl, aryl and benzyl;

M is a monovalent cation;
n, m and 1 are independently an integer between 1-5;
p and q are independently an integer between 1-6; and
X is an anion;
wherein if one of $R^5$-$R^7$ and $R^{5'}$-$R^{7'}$ is $SO_3^-$, then X is omitted.

In one embodiment, this invention is directed to a photoluminescent compound represented by the structure of formula (VII):

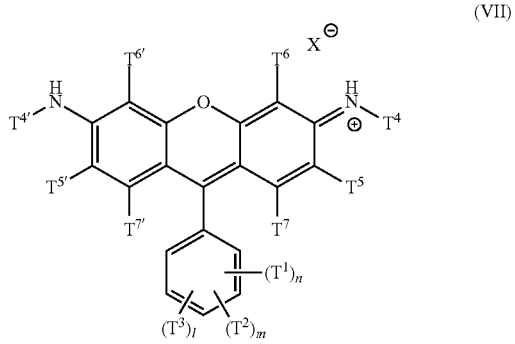

(VII)

wherein:
$T^1$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$T^2$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$T^3$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$T^4$ and $T^{4'}$ are each independently selected from alkyl, haloalkyl, heterocycloalkyl, cycloalkyl, aryl and benzyl;
$T^5$ and $T^{5'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide;
$T^6$, $T^{6'}$, $T^7$ and $T^{7'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide; or
$T^4$ and $T^5$ or $T^{4'}$ and $T^{5'}$ form together a N-heterocyclic ring wherein said ring is optionally substituted;
$Q^1$ and $Q^2$ are each independently selected from H, alkyl, haloalkyl, heterocycloalkyl, cycloalkyl, aryl, benzyl, —(CH$_2$)$_p$OC(O)NH(CH$_2$)$_q$Si(Oalkyl)$_3$, —(CH$_2$)$_p$OC(O)CH=CH$_2$, —(CH$_2$)$_p$Si(Oalkyl)$_3$, —OC(O)N(H)Q$^4$, —OC(S)N(H)Q$^4$, —N(H)C(O)N(Q$^3$)$_2$ and —N(H)C(S)N(Q$^3$)$_2$;
$Q^3$ and $Q^4$ are each independently selected from H, alkyl, haloalkyl, heterocycloalkyl, cycloalkyl, aryl and benzyl;
M is a monovalent cation;
n, m and 1 are independently an integer between 1-5;
p and q are independently an integer between 1-6; and
X is an anion;
wherein if one of $T^5$-$T^7$ and $T^{5'}$-$T^{7'}$ is $SO_3^-$, then X is omitted.

In one embodiment, this invention provides a photoluminescent device comprising a color-conversion-layer comprising a photoluminescent compound of this invention. In another embodiment, the photoluminescent device is integrated in a backlight unit of a LCD display. In another embodiment, the photoluminescent device comprises a compound of this invention having an emission peak between 520-560 nm and FWHM between 30-55 nm.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
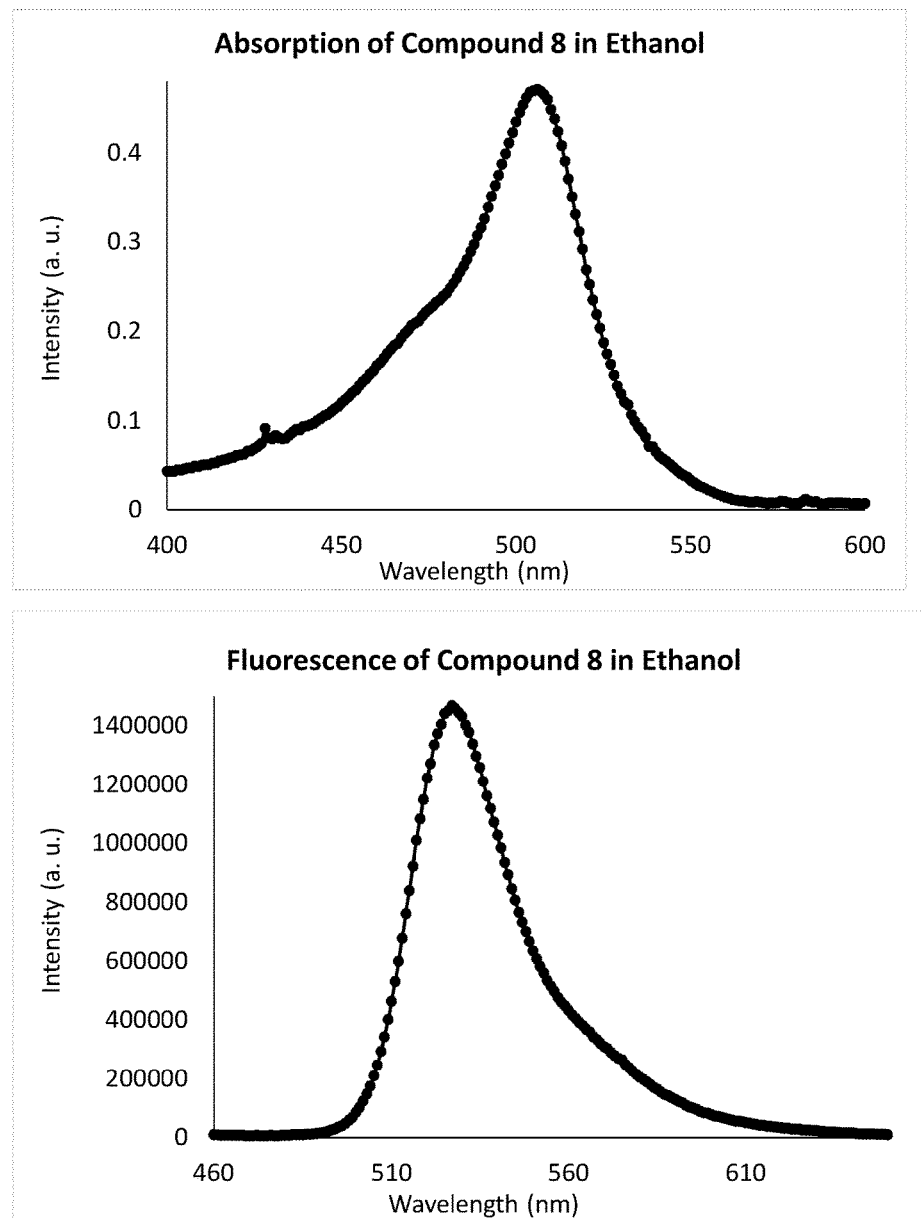
FIG. 1 depicts absorption and emission spectra of compound 8 in ethanol, wherein the compound absorbs at 506 nm and emits at 527 nm
Figure 2:
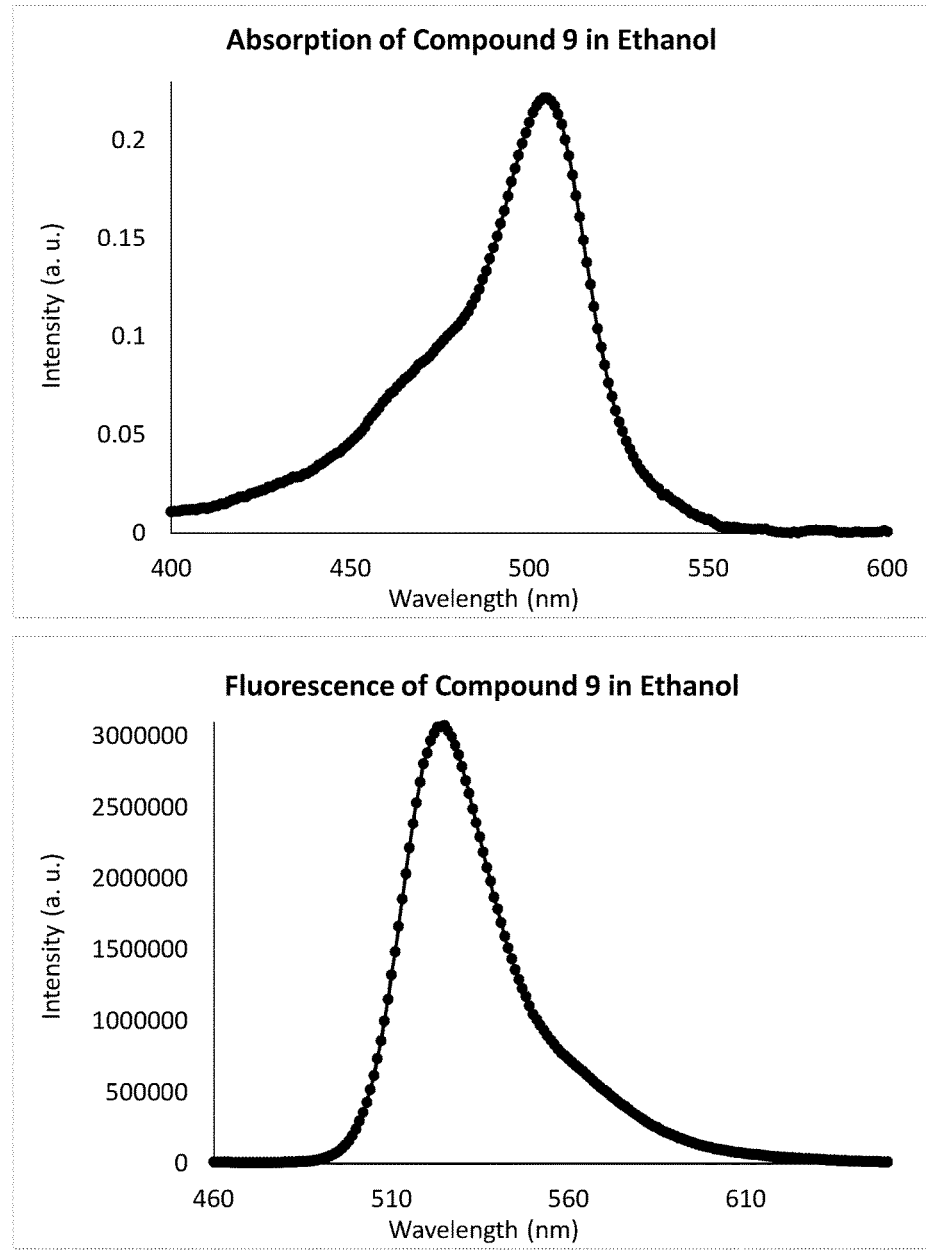
FIG. 2 depicts absorption and emission spectra of compound 9 in ethanol, wherein the compound absorbs at 505 nm and emits at 525 nm
Figure 3:
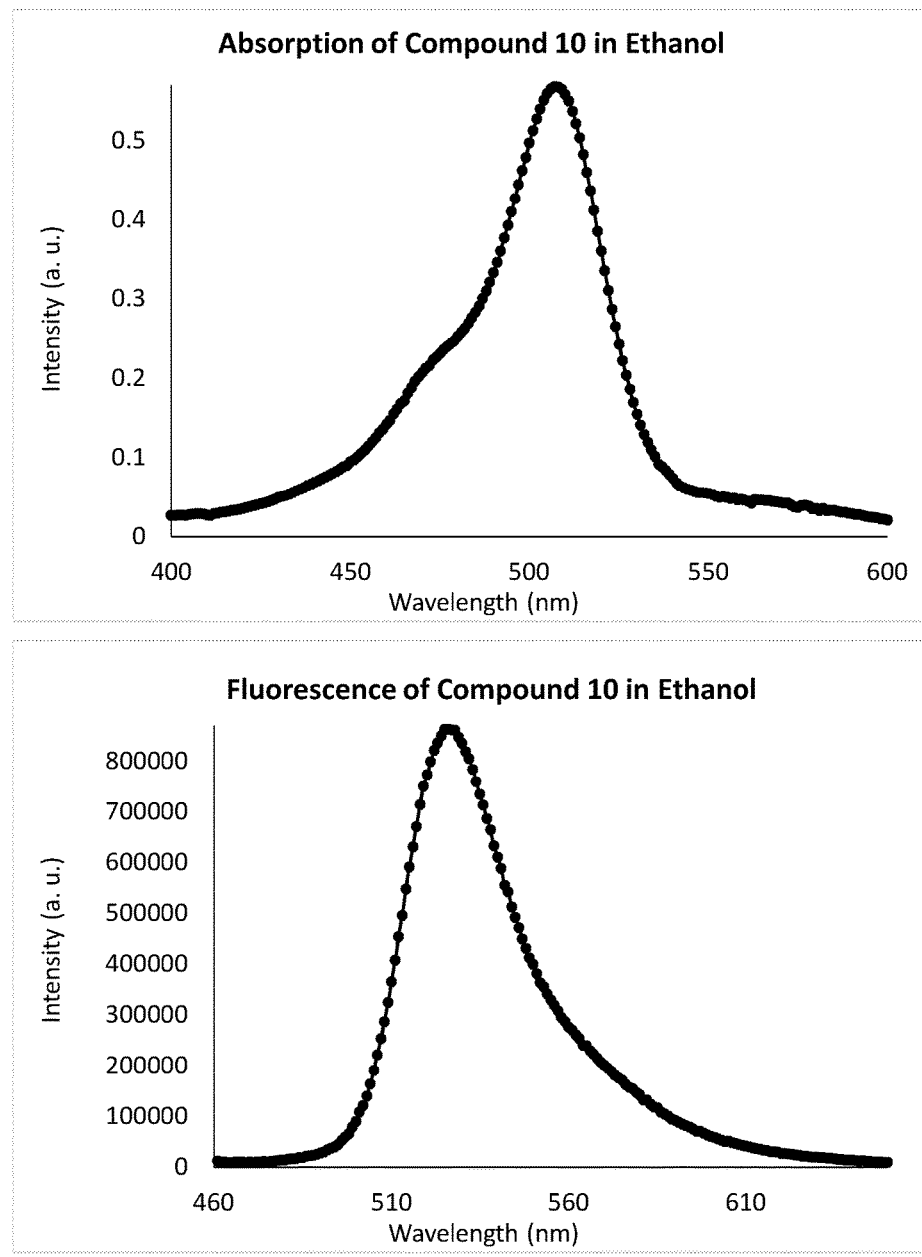
FIG. 3 depicts absorption and emission spectra of compound 10 in ethanol, wherein the compound absorbs at 507 nm and emits at 525 nm.
Figure 4:
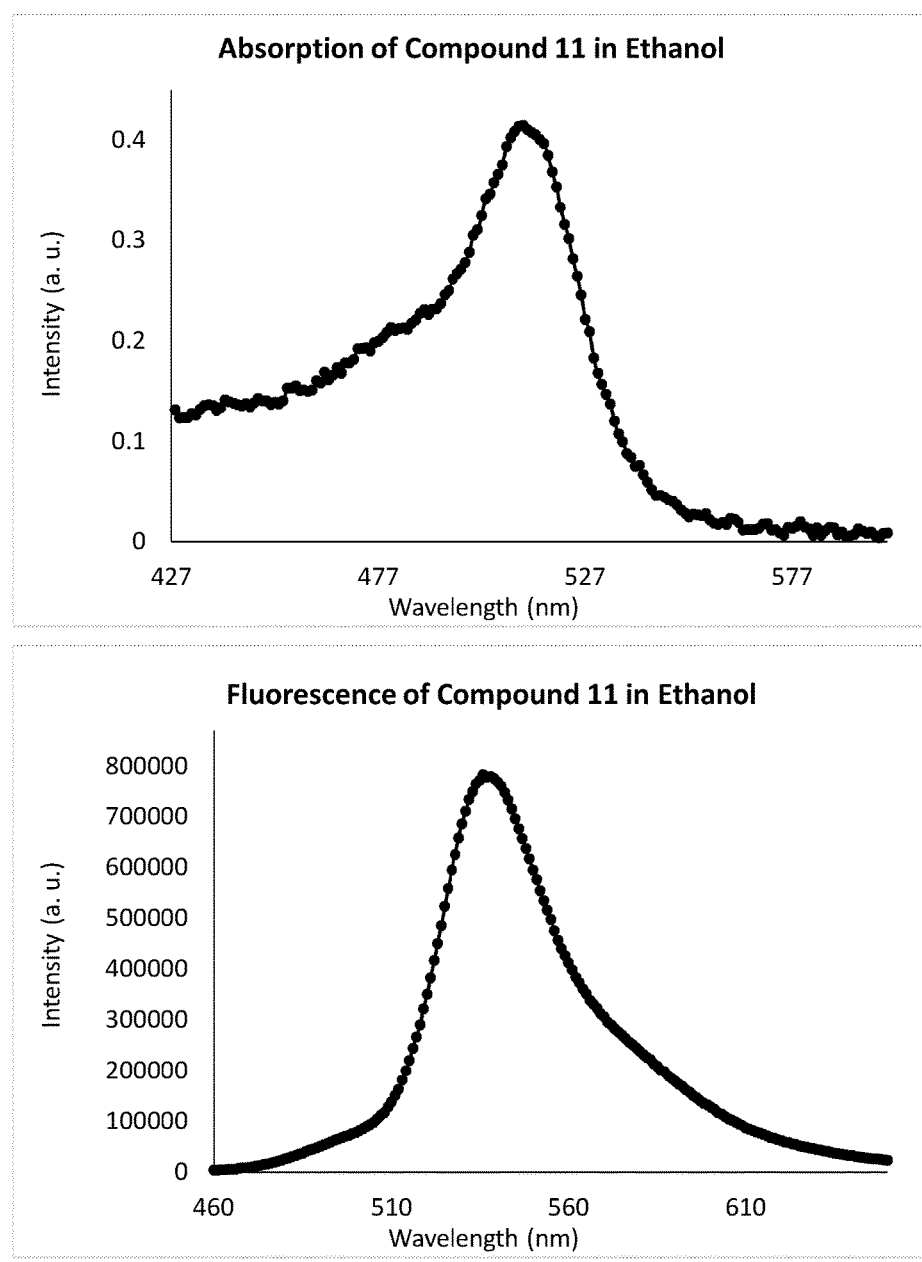
FIG. 4 depicts absorption and emission spectra of compound 11 in ethanol, wherein the compound absorbs at 512 nm and emits at 538 nm.
Figure 5:
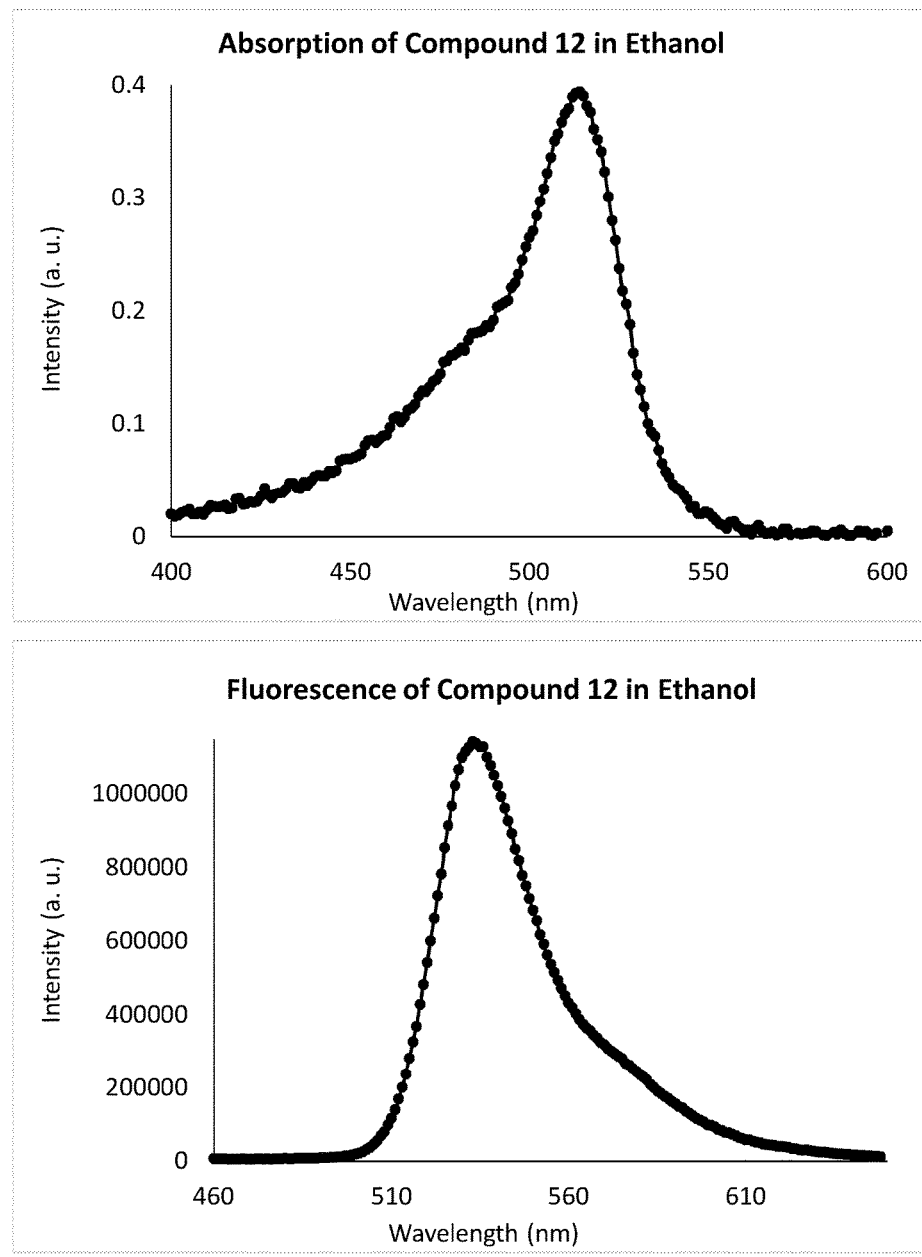
FIG. 5 depicts absorption and emission spectra of compound 12 in ethanol, wherein the compound absorbs at 514 nm and emits at 533 nm.
Figure 6:
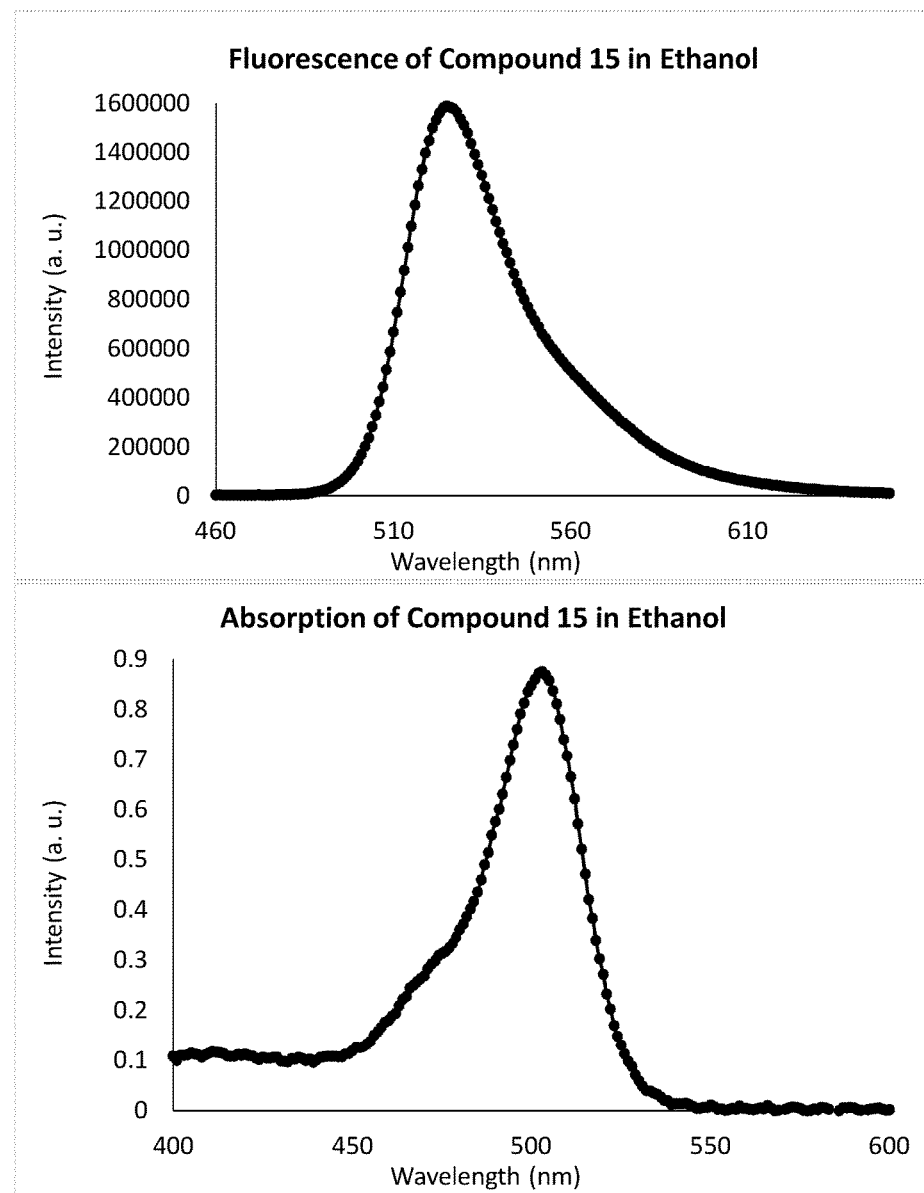
FIG. 6 depicts absorption and emission spectra of compound 15 in ethanol, wherein the compound absorbs at 503 nm and emits at 525 nm.
Figure 7:
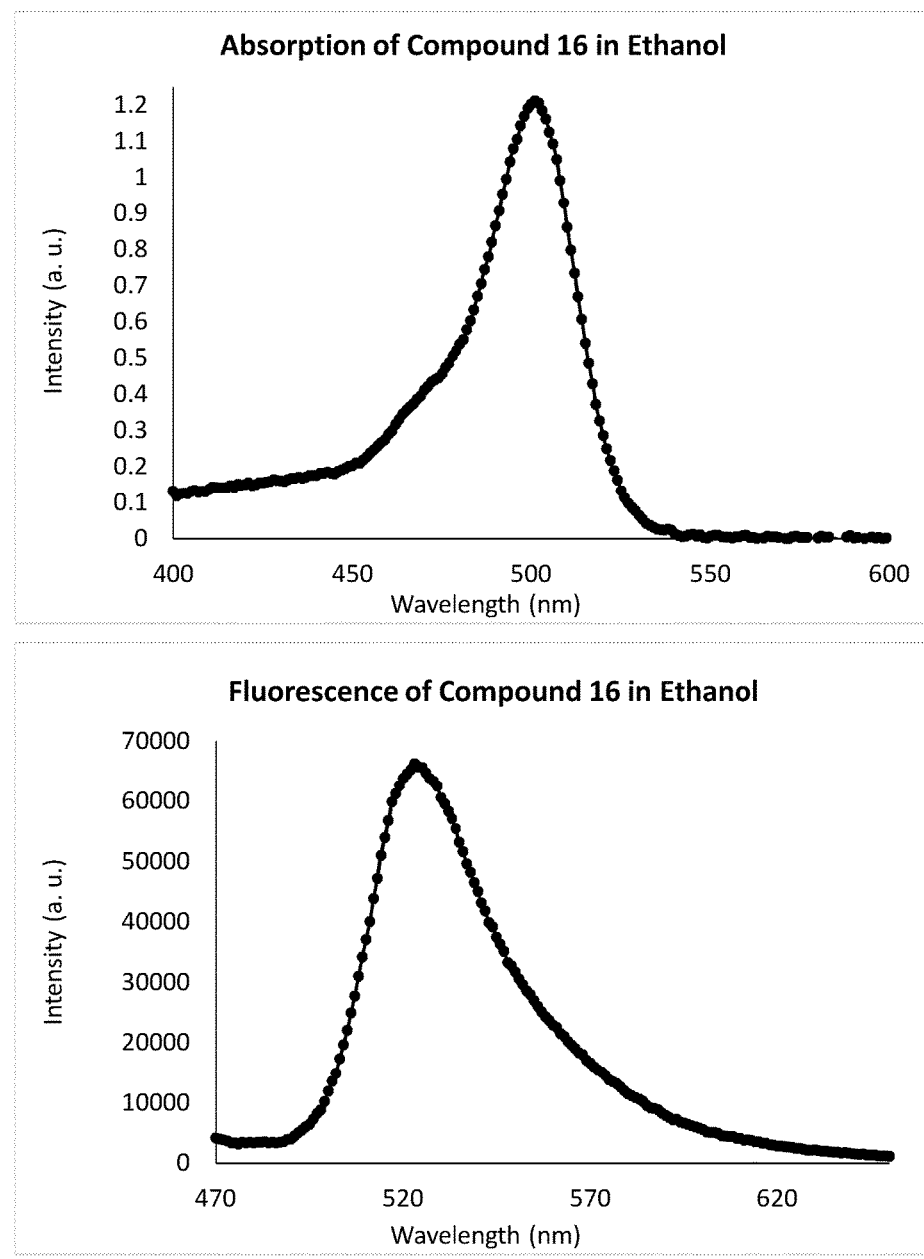
FIG. 7 depicts absorption and emission spectra of compound 16 in ethanol, wherein the compound absorbs at 501 nm and emits at 523 nm.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Photoluminescent materials refer to any material that absorbs light energy and then release that energy in the form of light. Two typical types of photoluminescence are: fluorescence and phosphorescence.

Fluorescent materials absorb light and then emit light instantaneously at a different wavelength, most of the times at a longer one. Fluorescent materials are used as light conversion emitters to modify the spectral response of light sources. Fluorescent compounds convert all or part of the light (depending on the absorbance coefficient and quantum yield of the molecule) absorbed in a certain energy interval to radiate it at longer wavelengths. This approach is used to fabricate or modify light sources that emit in the visible spectral range (light wavelengths between 400 and 800 nm). These latter sources are used in lighting devices that produce visible light. Examples of such lighting devices are fluorescent tubes, fluorescent compact lamps, or ultraviolet-based white light emitting diodes, where the ultraviolet radiation, invisible to the human eye, is converted by fluorescent materials into visible light (longer than UV) with a spectral distribution between 400 and 800 nm.

Phosphorescent materials absorb light of short wavelength and then emit light slowly over time also at a different, longer wavelength.

In one embodiment, this invention is directed to a photoluminescent compound.

In one embodiment, this invention is directed to a fluorescent compound.

In one embodiment, this invention is directed to photoluminescent compounds based on rhodamine dyes emitting at the green region of the visible spectrum.

Rhodamine having a carboxyphenyl fragment can be in one of three forms, depending on the pH, temperature, properties of the solvent, its polarity, and the concentration of the solution: cationic (+), zwitterion (±) or lactone.

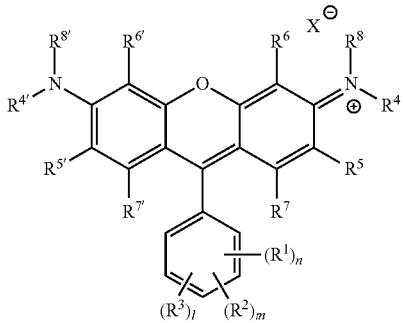

wherein
$R^1$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^2$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^3$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^4$, $R^{4'}$, $R^8$ and $R^{8'}$ are each independently selected from H, alkyl, haloalkyl, heterocycloalkyl, cycloalkyl, aryl and benzyl;
$R^5$ and $R^{5'}$ are each independently selected from Z, $OQ^1$, $CF_3$, $C(O)Q^1$, $COOQ^1$, $CON(Q^1)_2$, $NQ^1Q^2$, $NO_2$, CN,

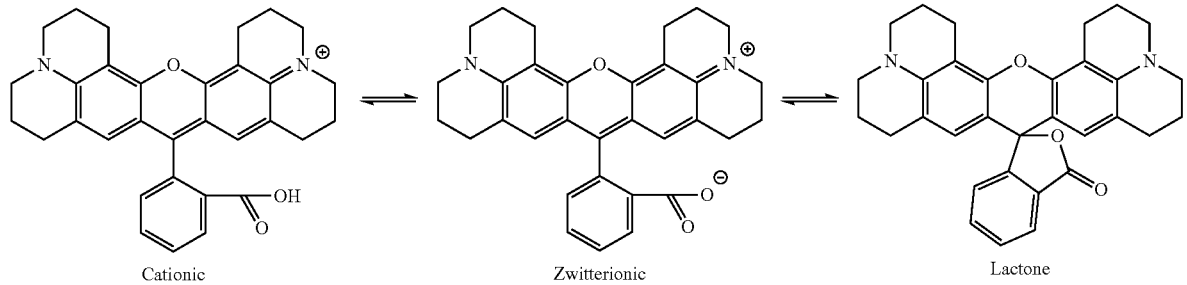 [SMILES: O=C(O)c1ccccc1C1=c2cc3c4c(c2Oc2c1cc1c5c2CCCN5CCC1)CCC[N+]=4CCC3 ; O=C([O-])c1ccccc1C1=c2cc3c4c(c2Oc2c1cc1c5c2CCCN5CCC1)CCC[N+]=4CCC3 ; O=C1OC2(c3ccccc31)c1cc3c4c(c1Oc1c2cc2c5c1CCCN5CCC2)CCCN4CCC3]

Cationic      Zwitterionic      Lactone

Each form has its own characteristic spectral-luminescent properties. While rhodamine derivatives in cationic and zwitterionic forms are highly fluorescent molecules, the lactone form is essentially non-fluorescent due to the interruption of π-conjugation of the chromophore of the zwitterionic form. Consequently, absorption of lactones of rhodamine occurs in the UV spectral region and the fluorescence quantum yield and lifetime are very low.

In one embodiment, the compounds of this invention do not form a lactone at the 3-position of a rhodamine derivative, by having a functional group different than carboxylic acid at position 3 of the rhodamine. In another embodiment, the compounds of this invention possess narrow FWHM values and high quantum yields.

In one embodiment, this invention is directed to a photoluminescent compound represented by the structure of formula (I):

$SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide;
$R^6$, $R^{6'}$, $R^7$ and $R^{7'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide; or
$R^4$ and $R^5$ or $R^{4'}$ and $R^{5'}$ form together a N-heterocyclic ring wherein said ring is optionally substituted;
$Q^1$ and $Q^2$ are each independently selected from H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —OC(O)N(H)$Q^4$, —OC(S)N(H)$Q^4$, —N(H)C(O)N($Q^3$)$_2$ and N(H)C(S)N($Q^3$)$_2$;
Z is selected from alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —OC(O)N(H)$Q^4$, —OC(S)N(H)$Q^4$, —N(H)C(O)N($Q^3$)$_2$ and —N(H)C(S)N($Q^3$)$_2$;
$Q^3$ and $Q^4$ are each independently selected from H, alkyl, haloalkyl, heterocycloalkyl, cycloalkyl, aryl and benzyl;

M is a monovalent cation;
n, m and l are independently an integer between 1-5;
p and q are independently an integer between 1-6; and
X is an anion;
wherein if one of $R^5$-$R^7$ and $R^{5'}$-$R^{7'}$ is $SO_3^-$, then X is omitted.

In one embodiment, this invention is directed to a photoluminescent compound represented by the structure of formula (II):

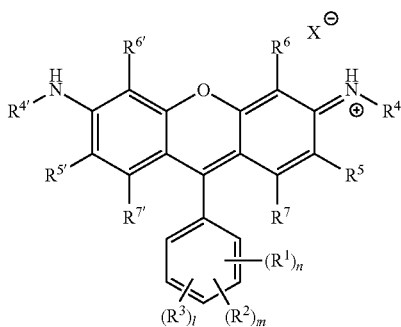

(II)

wherein
$R^1$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^2$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^3$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^4$ and $R^{4'}$ are each independently selected from H, alkyl, haloalkyl, heterocycloalkyl, cycloalkyl, aryl and benzyl;
$R^5$ and $R^{5'}$ are each independently selected from Z, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide;
$R^6$, $R^{6'}$, $R^7$ and $R^{7'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide; or
$R^4$ and $R^5$ or $R^{4'}$ and $R^{5'}$ form together a N-heterocyclic ring wherein said ring is optionally substituted;
$Q^1$ and $Q^2$ are each independently selected from H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and —$N(H)C(S)N(Q^3)_2$;
Z is selected from alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and —$N(H)C(S)N(Q^3)_2$;
$Q^3$ and $Q^4$ are each independently selected from H, alkyl, haloalkyl, heterocycloalkyl, cycloalkyl, aryl and benzyl;
M is a monovalent cation;
n, m and l are independently an integer between 1-5;
p and q are independently an integer between 1-6; and
X is an anion;
wherein if one of $R^5$-$R^7$ and $R^{5'}$-$R^{7'}$ is $SO_3^-$, then X is omitted.

In one embodiment, this invention is directed to a photoluminescent compound represented by the structure of formula (III):

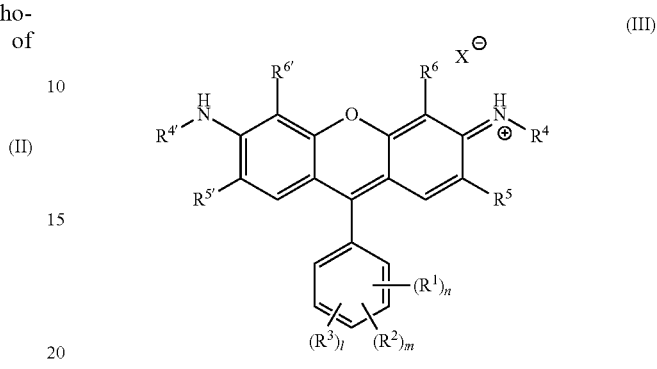

(III)

wherein
$R^1$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^2$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^3$ each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;
$R^4$ and $R^{4'}$ are each independently selected from H, alkyl, haloalkyl, heterocycloalkyl, cycloalkyl, aryl and benzyl;
$R^5$ and $R^{5'}$ are each independently selected from Z, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide;
$R^6$ and $R^{6'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide; or
$R^4$ and $R^5$ or $R^{4'}$ and $R^{5'}$ form together a N-heterocyclic ring wherein said ring is optionally substituted;
$Q^1$ and $Q^2$ are each independently selected from H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and $N(H)C(S)N(Q^3)_2$;
Z is selected from alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and —$N(H)C(S)N(Q^3)_2$;
$Q^3$ and $Q^4$ are each independently selected from H, alkyl, haloalkyl, heterocycloalkyl, cycloalkyl, aryl and benzyl;
M is a monovalent cation;
n, m and l are independently an integer between 1-5;
p and q are independently an integer between 1-6; and
X is an anion;
wherein if one of $R^5$-$R^6$ and $R^{5'}$-$R^{6'}$ is $SO_3^-$, then X is omitted.

In one embodiment, this invention is directed to a photoluminescent compound represented by the structure of formula (IV):

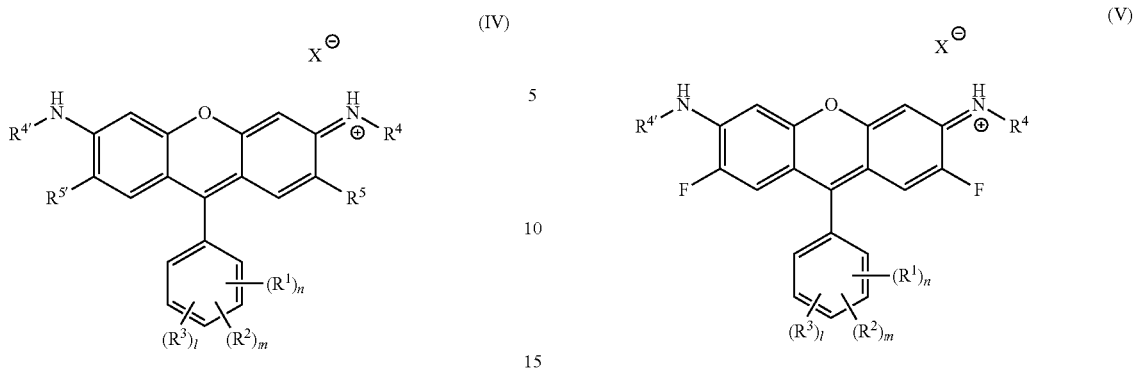

(IV)

wherein

R[1] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

R[2] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

R[3] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

$R^4$ and $R^{4'}$ are each independently selected from H, alkyl, haloalkyl, heterocycloalkyl, cycloalkyl, aryl and benzyl;

$R^5$ and $R^{5'}$ are each independently selected from Z, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide and halide; or $R^4$ and $R^5$ or $R^{4'}$ and $R^{5'}$ form together a N-heterocyclic ring wherein said ring is optionally substituted;

$Q^1$ and $Q^2$ are each independently selected from H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and —$N(H)C(S)N(Q^3)_2$;

Z is selected from alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and —$N(H)C(S)N(Q^3)_2$;

$Q^3$ and $Q^4$ are each independently selected from H, alkyl, haloalkyl, heterocycloalkyl, cycloalkyl, aryl and benzyl;

M is a monovalent cation;

n, m and l are independently an integer between 1-5;

p and q are independently an integer between 1-6; and

X is an anion;

wherein if one of $R^5$ and $R^{5'}$ is $SO_3^-$, then X is omitted.

In one embodiment, this invention is directed to a photoluminescent compound represented by the structure of formula (V):

(V)

wherein

R[1] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

R[2] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

R[3] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

$R^4$ and $R^{4'}$ are each independently selected from H, alkyl, haloalkyl, heterocycloalkyl, cycloalkyl, aryl and benzyl;

$Q^1$ and $Q^2$ are each independently selected from H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ and $N(H)C(S)N(Q^3)_2$;

$Q^3$ and $Q^4$ are each independently selected from H, alkyl, haloalkyl, heterocycloalkyl, cycloalkyl, aryl and benzyl;

n, m and l are independently an integer between 1-5;

p and q are independently an integer between 1-6; and

X is an anion.

In one embodiment, this invention is directed to a photoluminescent compound represented by the structure of formula (VI):

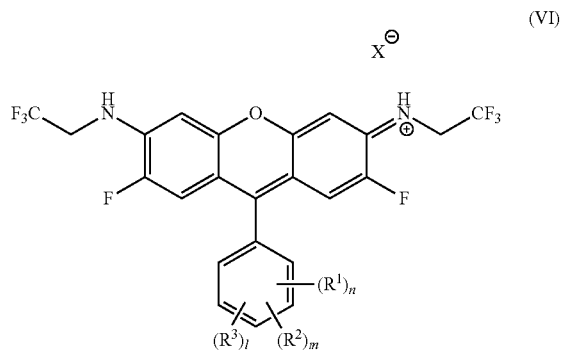

(VI)

wherein

R[1] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

R[2] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

R[3] each is independently H, $Q^1$, $OQ^1$, $CF_3$, $C(O)Q^1$, $NQ^1Q^2$, $NO_2$, CN, $SQ^1$, —$NQ^1Q^2CONQ^3Q^4$, NCO, NCS, —OC(O)$OQ^1$ or halide;

$Q^1$ and $Q^2$ are each independently selected from H, alkyl, haloalkyl, heterocycloalkyl, cycloalkyl, aryl, benzyl, —(CH$_2$)$_p$OC(O)NH(CH$_2$)$_q$Si(Oalkyl)$_3$, —(CH$_2$)$_p$OC(O)CH=CH$_2$, —(CH$_2$)$_p$Si(Oalkyl)$_3$, —OC(O)N(H)Q$^4$, —OC(S)N(H)Q$^4$, —N(H)C(O)N(Q$^3$)$_2$ and —N(H)C(S)N(Q$^3$)$_2$;

$Q^3$ and $Q^4$ are each independently selected from H, alkyl, haloalkyl, heterocycloalkyl, cycloalkyl, aryl and benzyl;

n, m and l are independently an integer between 1-5;

p and q are independently an integer between 1-6; and

X is an anion.

In one embodiment, this invention is directed to a photoluminescent compound represented by the structure of formula (VII):

(VII)

wherein $T^1$ each is independently H, Q$^1$, OQ$^1$, CF$_3$, C(O)Q$^1$, NQ$^1$Q$^2$, NO$_2$, CN, SQ$^1$, —NQ$^1$Q$^2$CONQ$^3$Q$^4$, NCO, NCS, —OC(O)OQ$^1$ or halide;

$T^2$ each is independently H, Q$^1$, OQ$^1$, CF$_3$, C(O)Q$^1$, NQ$^1$Q$^2$, NO$_2$, CN, SQ$^1$, —NQ$^1$Q$^2$CONQ$^3$Q$^4$, NCO, NCS, —OC(O)OQ$^1$ or halide;

$T^3$ each is independently H, Q$^1$, OQ$^1$, CF$_3$, C(O)Q$^1$, NQ$^1$Q$^2$, NO$_2$, CN, SQ$^1$, —NQ$^1$Q$^2$CONQ$^3$Q$^4$, NCO, NCS, —OC(O)OQ$^1$ or halide;

$T^4$ and $T^{4'}$ are each independently selected from alkyl, haloalkyl, heterocycloalkyl, cycloalkyl, aryl and benzyl;

$T^5$ and $T^{5'}$ are each independently selected from H, Q$^1$, OQ$^1$, CF$_3$, C(O)Q$^1$, COOQ$^1$, CON(Q$^1$)$_2$, NQ$^1$Q$^2$, NO$_2$, CN, SO$_3^-$, SO$_3$M, SO$_3$H, SQ$^1$, —NQ$^1$Q$^2$CONQ$^3$Q$^4$, NCO, NCS, alkenyl, alkynyl, epoxide, alkylated epoxide, azide and halide;

$T^6$, $T^{6'}$, $T^7$ and $T^{7'}$ are each independently selected from H, Q$^1$, OQ$^1$, CF$_3$, C(O)Q$^1$, COOQ$^1$, CON(Q$^1$)$_2$, NQ$^1$Q$^2$, NO$_2$, CN, SO$_3^-$, SO$_3$M, SO$_3$H, SQ$^1$, —NQ$^1$Q$^2$CONQ$^3$Q$^4$, NCO, NCS, alkenyl, alkynyl, epoxide, alkylated epoxide, azide and halide; or $T^4$ and $T^5$ or $T^{4'}$ and $T^{5'}$ form together a N-heterocyclic ring wherein said ring is optionally substituted;

$Q^1$ and $Q^2$ are each independently selected from H, alkyl, haloalkyl, heterocycloalkyl, cycloalkyl, aryl, benzyl, —(CH$_2$)$_p$OC(O)NH(CH$_2$)$_q$Si(Oalkyl)$_3$, —(CH$_2$)$_p$OC(O)CH=CH$_2$, —(CH$_2$)$_p$Si(Oalkyl)$_3$, —OC(O)N(H)Q$^4$, —OC(S)N(H)Q$^4$, —N(H)C(O)N(Q$^3$)$_2$ and —N(H)C(S)N(Q$^3$)$_2$;

$Q^3$ and $Q^4$ are each independently selected from H, alkyl, haloalkyl, heterocycloalkyl, cycloalkyl, aryl and benzyl;

M is a monovalent cation;

n, m and l are independently an integer between 1-5;

p and q are independently an integer between 1-6; and

X is an anion.

wherein if one of $T^5$-$T^7$ and $T^{5'}$-$T^{7'}$ is SO$_3^-$, then X is omitted.

In one embodiment, this invention is directed to a photoluminescent compound represented by the structure of formula (VIII):

(VIII)

wherein $T^1$ each is independently H, Q$^1$, OQ$^1$, CF$_3$, C(O)Q$^1$, NQ$^1$Q$^2$, NO$_2$, CN, SQ$^1$, —NQ$^1$Q$^2$CONQ$^3$Q$^4$, NCO, NCS, —OC(O)OQ$^1$ or halide;

$T^2$ each is independently H, Q$^1$, OQ$^1$, CF$_3$, C(O)Q$^1$, NQ$^1$Q$^2$, NO$_2$, CN, SQ$^1$, —NQ$^1$Q$^2$CONQ$^3$Q$^4$, NCO, NCS, —OC(O)OQ$^1$ or halide;

$T^3$ each is independently H, Q$^1$, OQ$^1$, CF$_3$, C(O)Q$^1$, NQ$^1$Q$^2$, NO$_2$, CN, SQ$^1$, —NQ$^1$Q$^2$CONQ$^3$Q$^4$, NCO, NCS, —OC(O)OQ$^1$ or halide;

$T^4$ and $T^{4'}$ are each independently selected from alkyl, haloalkyl, heterocycloalkyl, cycloalkyl, aryl and benzyl;

$T^5$ and $T^{5'}$ are each independently selected from H, Q$^1$, OQ$^1$, CF$_3$, C(O)Q$^1$, COOQ$^1$, CON(Q$^1$)$_2$, NQ$^1$Q$^2$, NO$_2$, CN, SO$_3^-$, SO$_3$M, SO$_3$H, SQ$^1$, —NQ$^1$Q$^2$CONQ$^3$Q$^4$, NCO, NCS, alkenyl, alkynyl, epoxide, alkylated epoxide, azide and halide;

$T^6$ and $T^{6'}$ are each independently selected from H, Q$^1$, OQ$^1$, CF$_3$, C(O)Q$^1$, COOQ$^1$, CON(Q$^1$)$_2$, NQ$^1$Q$^2$, NO$_2$, CN, SO$_3^-$, SO$_3$M, SO$_3$H, SQ$^1$, —NQ$^1$Q$^2$CONQ$^3$Q$^4$, NCO, NCS, alkenyl, alkynyl, epoxide, alkylated epoxide, azide and halide; or $T^4$ and $T^5$ or $T^{4'}$ and $T^{5'}$ form together a N-heterocyclic ring wherein said ring is optionally substituted;

$Q^1$ and $Q^2$ are each independently selected from H, alkyl, haloalkyl, heterocycloalkyl, cycloalkyl, aryl, benzyl, —(CH$_2$)$_p$OC(O)NH(CH$_2$)$_q$Si(Oalkyl)$_3$, —(CH$_2$)$_p$OC(O)CH=CH$_2$, —(CH$_2$)$_p$Si(Oalkyl)$_3$, —OC(O)N(H)Q$^4$, —OC(S)N(H)Q$^4$, —N(H)C(O)N(Q$^3$)$_2$ and —N(H)C(S)N(Q$^3$)$_2$;

$Q^3$ and $Q^4$ are each independently selected from H, alkyl, haloalkyl, heterocycloalkyl, cycloalkyl, aryl and benzyl;

M is a monovalent cation;

n, m and l are independently an integer between 1-5;

p and q are independently an integer between 1-6; and

X is an anion;

wherein if one of $T^5$-$T^6$ and $T^{5'}$-$T^{6'}$ is SO$_3^-$, then X is omitted.

In one embodiment, this invention is directed to a photoluminescent compound represented by the structure of formula (IX):

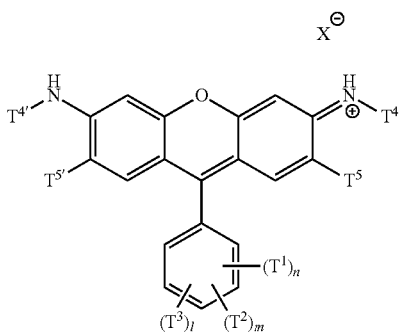

(IX)

wherein
T¹ each is independently H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide;
T² each is independently H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide;
T³ each is independently H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide;
T⁴ and T⁴' are each independently selected from alkyl, haloalkyl, heterocycloalkyl, cycloalkyl, aryl and benzyl;
T⁵ and T⁵' are each independently selected from H, Q¹, OQ¹, CF₃, C(O)Q¹, COOQ¹, CON(Q¹)₂, NQ¹Q², NO₂, CN, SO₃⁻, SO₃M, SO₃H, SQ¹, —NQ¹Q²CONQ³Q⁴, NCO, NCS, alkenyl, alkynyl, epoxide, alkylated epoxide, azide and halide; or
T⁴ and T⁵ or T⁴' and T⁵' form together a N-heterocyclic ring wherein said ring is optionally substituted;
Q¹ and Q² are each independently selected from H, alkyl, haloalkyl, heterocycloalkyl, cycloalkyl, aryl, benzyl, —(CH₂)ₚOC(O)NH(CH₂)_qSi(Oalkyl)₃, —(CH₂)ₚOC(O)CH=CH₂, —(CH₂)ₚSi(Oalkyl)₃, —OC(O)N(H)Q⁴, —OC(S)N(H)Q⁴, —N(H)C(O)N(Q³)₂ and —N(H)C(S)N(Q³)₂;
Q³ and Q⁴ are each independently selected from H, alkyl, haloalkyl, heterocycloalkyl, cycloalkyl, aryl and benzyl;
M is a monovalent cation;
n, m and l are independently an integer between 1-5;
p and q are independently an integer between 1-6; and
X is an anion;
wherein if one of T⁵ and T⁵' is SO₃⁻, then X is omitted.

In one embodiment, this invention is directed to a photoluminescent compound represented by the structure of formula (X):

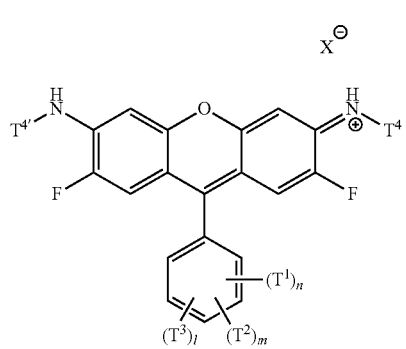

(X)

wherein
T¹ each is independently H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide;
T² each is independently H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide;
T³ each is independently H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide;
T⁴ and T⁴' are each independently selected from alkyl, haloalkyl, heterocycloalkyl, cycloalkyl, aryl and benzyl;
Q¹ and Q² are each independently selected from H, alkyl, haloalkyl, heterocycloalkyl, cycloalkyl, aryl, benzyl, —(CH₂)ₚOC(O)NH(CH₂)_qSi(Oalkyl)₃, —(CH₂)ₚOC(O)CH=CH₂, —(CH₂)ₚSi(Oalkyl)₃, —OC(O)N(H)Q⁴, —OC(S)N(H)Q⁴, —N(H)C(O)N(Q³)₂ and —N(H)C(S)N(Q³)₂;
Q³ and Q⁴ are each independently selected from H, alkyl, haloalkyl, heterocycloalkyl, cycloalkyl, aryl and benzyl;
M is a monovalent cation;
n, m and l are independently an integer between 1-5;
p and q are independently an integer between 1-6; and
X is an anion.

In one embodiment, R¹ of formula I-VI is H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide. In another embodiment, R¹ is H. In another embodiment, R¹ is Q¹. In another embodiment, R¹ is OQ¹. In another embodiment, R¹ is CF₃. In another embodiment, R¹ is C(O)Q¹ In another embodiment, R¹ is NQ¹Q². In another embodiment, R¹ is NO₂. In another embodiment, R¹ is CN. In another embodiment, R¹ is SQ¹. In another embodiment R¹ is —NQ¹Q²CONQ³Q⁴. In another embodiment, R¹ is NCO. In another embodiment, R¹ is NCS. In another embodiment, R¹ is, —OC(O)OQ¹. In another embodiment, R¹ is halide.

In one embodiment, R² of formula I-VI is H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide. In another embodiment, R² is H. In another embodiment, R² is Q¹. In another embodiment, R² is OQ¹. In another embodiment, R² is CF₃. In another embodiment, R² is C(O)Q¹ In another embodiment, R² is NQ¹Q². In another embodiment, R² is NO₂. In another embodiment, R² is CN. In another embodiment, R² is SQ¹. In another embodiment R² is —NQ¹Q²CONQ³Q⁴. In another embodiment, R² is NCO. In another embodiment, R² is NCS. In another embodiment, R² is, —OC(O)OQ¹. In another embodiment, R² is halide.

In one embodiment, R³ of formula I-VI is H, Q¹, OQ¹, CF₃, C(O)Q¹, NQ¹Q², NO₂, CN, SQ¹, —NQ¹Q²CONQ³Q⁴, NCO, NCS, —OC(O)OQ¹ or halide. In another embodiment, R³ is H. In another embodiment, R³ is Q¹. In another embodiment, R³ is OQ¹. In another embodiment, R³ is CF₃. In another embodiment, R³ is C(O)Q¹ In another embodiment, R³ is NQ¹Q². In another embodiment, R³ is NO₂. In another embodiment, R³ is CN. In another embodiment, R³ is SQ¹. In another embodiment R³ is —NQ¹Q²CONQ³Q⁴. In another embodiment, R³ is NCO. In another embodiment, R³ is NCS. In another embodiment, R³ is —OC(O)OQ¹. In another embodiment, R³ is halide.

In one embodiment, Q¹ of formula I-X is H, alkyl, haloalkyl, heterocycloalkyl, cycloalkyl, aryl, benzyl, —(CH₂)ₚOC(O)NH(CH₂)_qSi(Oalkyl)₃, —(CH₂)ₚOC(O)CH=CH₂, —(CH₂)ₚSi(Oalkyl)₃, —OC(O)N(H)Q⁴, —OC(S)N(H)Q⁴, —N(H)C(O)N(Q³)₂ or —N(H)C(S)N(Q³)₂. In another embodiment, Q¹ is H. In another embodiment, Q¹ is alkyl. In another embodiment, Q¹ is haloalkyl. In another embodiment, $Q^1$ is heterocycloalkyl. In another embodiment, $Q^1$ is cycloalkyl. In another embodiment, $Q^1$ is aryl. In another embodiment, $Q^1$ is benzyl. In another embodiment, $Q^1$ is —$(CH_2)_pOC(O)NH(CH_2)_qSi(Oalkyl)_3$. In another embodiment, $Q^1$ is —$(CH_2)_pOC(O)CH=CH_2$. In another embodiment, $Q^1$ is —$(CH_2)_pSi(Oalkyl)_3$. In another embodiment, $Q^1$ is —$OC(O)N(H)Q^4$. In another embodiment, $Q^1$ is —$OC(S)N(H)Q^4$. In another embodiment, $Q^1$ is $N(H)C(O)N(Q^3)_2$. In another embodiment, $Q^1$ is —$N(H)C(S)N(Q^3)_2$.

In one embodiment, $Q^2$ of formula I-X is H, alkyl, haloalkyl, heterocycloalkyl, cycloalkyl, aryl, benzyl, —$(CH_2)_pOC(O)NH(CH_2)_qSi(Oalkyl)_3$, —$(CH_2)_pOC(O)CH=CH_2$, —$(CH_2)_pSi(Oalkyl)_3$, —$OC(O)N(H)Q^4$, —$OC(S)N(H)Q^4$, —$N(H)C(O)N(Q^3)_2$ or —$N(H)C(S)N(Q^3)_2$. In another embodiment, $Q^2$ is H. In another embodiment, $Q^2$ is alkyl. In another embodiment, $Q^2$ is haloalkyl. In another embodiment, $Q^2$ is heterocycloalkyl. In another embodiment, $Q^2$ is cycloalkyl. In another embodiment, $Q^2$ is aryl. In another embodiment, $Q^2$ is benzyl. In another embodiment, $Q^2$ is —$(CH_2)_pOC(O)NH(CH_2)_qSi(Oalkyl)_3$. In another embodiment, $Q^2$ is —$(CH_2)_pOC(O)CH=CH_2$. In another embodiment, $Q^2$ is —$(CH_2)_pSi(Oalkyl)_3$. In another embodiment, $Q^2$ is —$OC(O)N(H)Q^4$. In another embodiment, $Q^2$ is —$OC(S)N(H)Q^4$. In another embodiment, $Q^2$ is $N(H)C(O)N(Q^3)_2$. In another embodiment, $Q^2$ is —$N(H)C(S)N(Q^3)_2$.

In one embodiment, $Q^3$ of formula I-X is H, alkyl, haloalkyl, heterocycloalkyl, cycloalkyl, aryl or benzyl. In another embodiment, $Q^3$ is H. In another embodiment, $Q^3$ is alkyl. In another embodiment, $Q^3$ is fluorinated alkyl. In another embodiment, $Q^3$ is heterocycloalkyl. In another embodiment $Q^3$ is cycloalkyl. In another embodiment, $Q^3$ is aryl. In another embodiment, $Q^3$ is benzyl.

In one embodiment, $Q^4$ of formula I-X is H, alkyl, haloalkyl, heterocycloalkyl, cycloalkyl, aryl or benzyl. In another embodiment, $Q^4$ is H. In another embodiment, $Q^4$ is alkyl. In another embodiment, $Q^4$ is fluorinated alkyl. In another embodiment, $Q^4$ is heterocycloalkyl. In another embodiment $Q^4$ is cycloalkyl. In another embodiment, $Q^4$ is aryl. In another embodiment, $Q^4$ is benzyl.

In one embodiment, $R^4$ of formula I-VI is H, alkyl, haloalkyl, heterocycloalkyl, cycloalkyl, aryl or benzyl. In another embodiment, $R^4$ is H. In another embodiment, $R^4$ is alkyl. In another embodiment, $R^4$ is haloalkyl. In another embodiment, $R^4$ is heterocycloalkyl. In another embodiment, $R^4$ is cycloalkyl. In another embodiment, $R^4$ is aryl. In another embodiment, $R^4$ is benzyl.

In one embodiment, $R^{4'}$ of formula I-VI is H, alkyl, haloalkyl, heterocycloalkyl, cycloalkyl, aryl or benzyl. In another embodiment, $R^{4'}$ is H. In another embodiment, $R^{4'}$ is alkyl. In another embodiment, $R^{4'}$ is haloalkyl. In another embodiment, $R^{4'}$ is heterocycloalkyl. In another embodiment, $R^{4'}$ is cycloalkyl. In another embodiment, $R^{4'}$ is aryl. In another embodiment, $R^{4'}$ is benzyl.

In one embodiment, $R^5$ of formula I-V is Z, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $R^5$ is Z. In another embodiment, $R^5$ is $OQ^1$. In another embodiment, $R^5$ is $CF_3$. In another embodiment, $R^5$ is $C(O)Q^1$. In another embodiment, $R^5$ is $COOQ^1$. In another embodiment, $R^5$ is $CON(Q^1)_2$. In another embodiment, $R^5$ is $NQ^1Q^2$. In another embodiment, $R^5$ is $NO_2$. In another embodiment, $R^5$ is CN. In another embodiment, $R^5$ is $SO_3^-$. In another embodiment, $R^5$ is $SO_3M$. In another embodiment, $R^5$ is $SO_3H$. In another embodiment, $R^5$ is $SQ^1$. In another embodiment, $R^5$ is, —$NQ^1Q^2CONQ^3Q^4$. In another embodiment, $R^5$ is NCO. In another embodiment, $R^5$ is NCS. In another embodiment, $R^5$ is alkenyl. In another embodiment, $R^5$ is alkynyl. In another embodiment, $R^5$ is epoxide. In another embodiment, $R^5$ is alkylated epoxide. In another embodiment, $R^5$ is azide. In another embodiment, $R^5$ is halide.

In one embodiment, $R^{5'}$ of formula I-V is Z, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $R^{5'}$ is Z. In another embodiment, $R^{5'}$ is $OQ^1$. In another embodiment, $R^{5'}$ is $CF_3$. In another embodiment, $R^{5'}$ is $C(O)Q^1$. In another embodiment, $R^{5'}$ is $COOQ^1$. In another embodiment, $R^{5'}$ is $CON(Q^1)_2$. In another embodiment, $R^{5'}$ is $NQ^1Q^2$. In another embodiment, $R^{5'}$ is $NO_2$. In another embodiment, $R^{5'}$ is CN. In another embodiment, $R^{5'}$ is $SO_3^-$. In another embodiment, $R^{5'}$ is $SO_3M$. In another embodiment, $R^{5'}$ is $SO_3H$. In another embodiment, $R^{5'}$ is $SQ^1$. In another embodiment, $R^{5'}$ is, —$NQ^1Q^2CONQ^3Q^4$. In another embodiment, $R^{5'}$ is NCO. In another embodiment, $R^{5'}$ is NCS. In another embodiment, $R^{5'}$ is alkenyl. In another embodiment, $R^{5'}$ is alkynyl. In another embodiment, $R^{5'}$ is epoxide. In another embodiment, $R^{5'}$ is alkylated epoxide. In another embodiment, $R^{5'}$ is azide. In another embodiment, $R^{5'}$ is halide.

In one embodiment, $R^6$ of formula I-III is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $R^6$ is H. In another embodiment, $R^6$ is $Q^1$. In another embodiment, $R^6$ is $OQ^1$. In another embodiment, $R^6$ is $CF_3$. In another embodiment, $R^6$ is $C(O)Q^1$. In another embodiment, $R^6$ is $COOQ^1$. In another embodiment, $R^6$ is $CON(Q^1)_2$. In another embodiment, $R^6$ is $NQ^1Q^2$. In another embodiment, $R^6$ is $NO_2$. In another embodiment, $R^6$ is CN. In another embodiment, $R^6$ is $SO_3^-$. In another embodiment, $R^6$ is $SO_3M$. In another embodiment, $R^6$ is $SO_3H$. In another embodiment, $R^6$ is $SQ^1$. In another embodiment, $R^6$ is, —$NQ^1Q^2CONQ^3Q^4$. In another embodiment, $R^6$ is NCO. In another embodiment, $R^6$ is NCS. In another embodiment, $R^6$ is alkenyl. In another embodiment, $R^6$ is alkynyl. In another embodiment, $R^6$ is epoxide. In another embodiment, $R^6$ is alkylated epoxide. In another embodiment, $R^6$ is azide. In another embodiment, $R^6$ is halide.

In one embodiment, $R^{6'}$ of formula I-III is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $R^{6'}$ is H. In another embodiment, $R^{6'}$ is $Q^1$. In another embodiment, $R^{6'}$ is $OQ^1$. In another embodiment, $R^{6'}$ is $CF_3$. In another embodiment, $R^{6'}$ is $C(O)Q^1$. In another embodiment, $R^{6'}$ is $COOQ^1$. In another embodiment, $R^{6'}$ is $CON(Q^1)_2$. In another embodiment, $R^{6'}$ is $NQ^1Q^2$. In another embodiment, $R^{6'}$ is $NO_2$. In another embodiment, $R^{6'}$ is CN. In another embodiment, $R^{6'}$ is $SO_3^-$. In another embodiment, $R^{6'}$ is $SO_3M$. In another embodiment, $R^{6'}$ is $SO_3H$. In another embodiment, $R^{6'}$ is $SQ^1$. In another embodiment, $R^{6'}$ is, —$NQ^1Q^2CONQ^3Q^4$. In another embodiment, $R^{6'}$ is NCO. In another embodiment, $R^{6'}$ is NCS. In another embodiment, $R^{6'}$ is alkenyl. In another embodiment, $R^{6'}$ is alkynyl. In another embodiment, $R^{6'}$ is epoxide. In another embodiment, $R^{6'}$ is alkylated epoxide. In another embodiment, $R^{6'}$ is azide. In another embodiment, $R^{6'}$ is halide.

In one embodiment, $R^7$ of formula I-II is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, $-NQ^1Q^2CONQ^3Q^4$, NCO, NCS, alkenyl, alkynyl, epoxide, alkylated epoxide, azide or halide. In another embodiment, $R^7$ is H. In another embodiment, $R^7$ is $Q^1$. In another embodiment, $R^7$ is $OQ^1$. In another embodiment, $R^7$ is $CF_3$. In another embodiment, $R^7$ is $C(O)Q^1$. In another embodiment, $R^7$ is $COOQ^1$. In another embodiment, $R^7$ is $CON(Q^1)_2$. In another embodiment, $R^7$ is $NQ^1Q^2$. In another embodiment, $R^7$ is $NO_2$. In another embodiment, $R^7$ is CN. In another embodiment, $R^7$ is $SO_3^-$. In another embodiment, $R^7$ is $SO_3M$. In another embodiment, $R^7$ is $SO_3H$. In another embodiment, $R^7$ is $SQ^1$. In another embodiment, $R^7$ is, $-NQ^1Q^2CONQ^3Q^4$. In another embodiment, $R^7$ is NCO. In another embodiment, $R^7$ is NCS. In another embodiment, $R^7$ is alkenyl. In another embodiment, $R^7$ is alkynyl. In another embodiment, $R^7$ is epoxide. In another embodiment, $R^7$ is alkylated epoxide. In another embodiment, $R^7$ is azide. In another embodiment, $R^7$ is halide.

In one embodiment, $R^{7'}$ of formula I-II is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, $-NQ^1Q^2CONQ^3Q^4$, NCO, NCS, alkenyl, alkynyl, epoxide, alkylated epoxide, azide or halide. In another embodiment, $R^{7'}$ is H. In another embodiment, $R^{7'}$ is $Q^1$. In another embodiment, $R^{7'}$ is $OQ^1$. In another embodiment, $R^{7'}$ is $CF_3$. In another embodiment, $R^{7'}$ is $C(O)Q^1$. In another embodiment, $R^{7'}$ is $COOQ^1$. In another embodiment, $R^{7'}$ is $CON(Q^1)_2$. In another embodiment, $R^{7'}$ is $NQ^1Q^2$. In another embodiment, $R^{7'}$ is $NO_2$. In another embodiment, $R^{7'}$ is CN. In another embodiment, $R^{7'}$ is $SO_3^-$. In another embodiment, $R^{7'}$ is $SO_3M$. In another embodiment, $R^{7'}$ is $SO_3H$. In another embodiment, $R^{7'}$ is $SQ^1$. In another embodiment, $R^{7'}$ is, $-NQ^1Q^2CONQ^3Q^4$. In another embodiment, $R^{7'}$ is NCO. In another embodiment, $R^{7'}$ is NCS. In another embodiment, $R^{7'}$ is alkenyl. In another embodiment, $R^{7'}$ is alkynyl. In another embodiment, $R^{7'}$ is epoxide. In another embodiment, $R^{7'}$ is alkylated epoxide. In another embodiment, $R^{7'}$ is azide. In another embodiment, $R^{7'}$ is halide.

In one embodiment, $R^8$ of formula I is H, alkyl, haloalkyl, heterocycloalkyl, cycloalkyl, aryl or benzyl. In another embodiment, $R^8$ is H. In another embodiment, $R^8$ is alkyl. In another embodiment, $R^8$ is fluorinated alkyl. In another embodiment, $R^8$ is heterocycloalkyl. In another embodiment, $R^8$ is cycloalkyl. In another embodiment, $R^8$ is aryl. In another embodiment, $R^8$ is benzyl.

In one embodiment, $R^{8'}$ of formula I is H, alkyl, haloalkyl, heterocycloalkyl, cycloalkyl, aryl or benzyl. In another embodiment, $R^{8'}$ is H. In another embodiment, $R^{8'}$ is alkyl. In another embodiment, $R^{8'}$ is fluorinated alkyl. In another embodiment, $R^{8'}$ is heterocycloalkyl. In another embodiment, $R^{8'}$ is cycloalkyl. In another embodiment, $R^{8'}$ is aryl. In another embodiment, $R^{8'}$ is benzyl.

In one embodiment, $R^4$ and $R^5$ form together a N-heterocyclic ring wherein said ring is optionally substituted. In another embodiment, the N-heterocyclic ring is substituted by one or more groups selected from halide, hydroxy, alkoxy, carboxylic acid, aldehyde, carbonyl, amido, cyano, nitro, amino, alkenyl, alkynyl, aryl, azide, epoxide, ester, acyl chloride and thiol.

In one embodiment, $R^{4'}$ and $R^{5'}$ form together a N-heterocyclic ring wherein said ring is optionally substituted. In another embodiment, the N-heterocyclic ring is substituted by one or more groups selected from halide, hydroxy, alkoxy, carboxylic acid, aldehyde, carbonyl, amido, cyano, nitro, amino, alkenyl, alkynyl, aryl, azide, epoxide, ester, acyl chloride and thiol.

In one embodiment, Z of formula I-IV is selected from Z is selected from alkyl, haloalkyl, heterocycloalkyl, cycloalkyl, aryl, benzyl, $-(CH_2)_pOC(O)NH(CH_2)_qSi(Oalkyl)_3$, $-(CH_2)_pOC(O)CH=CH_2$, $-(CH_2)_pSi(Oalkyl)_3$, $-OC(O)N(H)Q^4$, $-OC(S)N(H)Q^4$, $-N(H)C(O)N(Q^3)_2$ and $-N(H)C(S)N(Q^3)_2$. In another embodiment, Z is alkyl. In another embodiment, Z is haloalkyl. In another embodiment, Z is heterocycloalkyl. In another embodiment, Z is cycloalkyl. In another embodiment, Z is aryl. In another embodiment, Z is benzyl. In another embodiment, Z is $-(CH_2)_pOC(O)NH(CH_2)_qSi(Oalkyl)_3$. In another embodiment, Z is $-(CH_2)_pOC(O)CH=CH_2$. In another embodiment, Z is $-(CH_2)_pSi(Oalkyl)_3$. In another embodiment, Z is $-OC(O)N(H)Q^4$. In another embodiment, Z is $-OC(S)N(H)Q^4$. In another embodiment, Z is $-N(H)C(O)N(Q^3)_2$. In another embodiment, Z is $-N(H)C(S)N(Q^3)_2$.

In one embodiment, $T^1$ of formula VII-X is H, $Q^1$, $OQ^1$, $CF_3$, $C(O)Q^1$, $NQ^1Q^2$, $NO_2$, CN, $SQ^1$, $-NQ^1Q^2CONQ^3Q^4$, NCO, NCS, $-OC(O)OQ^1$ or halide. In another embodiment, $T^1$ is H. In another embodiment, $T^1$ is $Q^1$. In another embodiment, $T^1$ is $OQ^1$. In another embodiment, $T^1$ is $CF_3$. In another embodiment, $T^1$ is $C(O)Q^1$. In another embodiment, $T^1$ is $NQ^1Q^2$. In another embodiment, $T^1$ is $NO_2$. In another embodiment, $T^1$ is CN. In another embodiment, $T^1$ is $SQ^1$. In another embodiment $T^1$ is $-NQ^1Q^2CONQ^3Q^4$. In another embodiment, $T^1$ is NCO. In another embodiment, $T^1$ is NCS. In another embodiment, $T^1$ is $-OC(O)OQ^1$. In another embodiment, $T^1$ is halide.

In one embodiment, $T^2$ of formula VII-X is H, $Q^1$, $OQ^1$, $CF_3$, $C(O)Q^1$, $NQ^1Q^2$, $NO_2$, CN, $SQ^1$, $-NQ^1Q^2CONQ^3Q^4$, NCO, NCS, $-OC(O)OQ^1$ or halide. In another embodiment, $T^2$ is H. In another embodiment, $T^2$ is $Q^1$. In another embodiment, $T^2$ is $OQ^1$. In another embodiment, $T^2$ is $CF_3$. In another embodiment, $T^2$ is $C(O)Q^1$ In another embodiment, $T^2$ is $NQ^1Q^2$. In another embodiment, $T^2$ is $NO_2$. In another embodiment, $T^2$ is CN. In another embodiment, $T^2$ is $SQ^1$. In another embodiment $T^2$ is $-NQ^1Q^2CONQ^3Q^4$. In another embodiment, $T^2$ is NCO. In another embodiment, $T^2$ is NCS. In another embodiment, $T^2$ is $-OC(O)OQ^1$. In another embodiment, $T^2$ is halide.

In one embodiment, $T^3$ of formula VII-X is H, $Q^1$, $OQ^1$, $CF_3$, $C(O)Q^1$, $NQ^1Q^2$, $NO_2$, CN, $SQ^1$, $-NQ^1Q^2CONQ^3Q^4$, NCO, NCS, $-OC(O)OQ^1$ or halide. In another embodiment, $T^3$ is H. In another embodiment, $T^3$ is $Q^1$. In another embodiment, $T^3$ is $OQ^1$. In another embodiment, $T^2$ is $CF_3$. In another embodiment, $T^3$ is $C(O)Q^1$ In another embodiment, $T^3$ is $NQ^1Q^2$. In another embodiment, $T^3$ is $NO_2$. In another embodiment, $T^3$ is CN. In another embodiment, $T^3$ is $SQ^1$. In another embodiment $T^3$ is $-NQ^1Q^2CONQ^3Q^4$. In another embodiment, $T^3$ is NCO. In another embodiment, $T^3$ is NCS. In another embodiment, $T^3$ is $-OC(O)OQ^1$. In another embodiment, $T^3$ is halide.

In one embodiment, $T^4$ of formula VII-X is alkyl, halo alkyl, heterocycloalkyl, cycloalkyl, aryl or benzyl. In another embodiment, $T^4$ is alkyl. In another embodiment, $T^4$ is haloalkyl. In another embodiment, $T^4$ is heterocycloalkyl. In another embodiment, $T^4$ is cycloalkyl. In another embodiment, $T^4$ is aryl. In another embodiment, $T^4$ is benzyl.

In one embodiment, $T^{4'}$ of formula VII-X is alkyl, halo alkyl, heterocycloalkyl, cycloalkyl, aryl or benzyl. In another embodiment, $T^{4'}$ is alkyl. In another embodiment, $T^{4'}$ is haloalkyl. In another embodiment, $T^{4'}$ is heterocycloalkyl. In another embodiment, $T^{4'}$ is cycloalkyl. In another embodiment, $T^{4'}$ is aryl. In another embodiment, $T^{4'}$ is benzyl.

In one embodiment, $T^5$ of formula VII-IX is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $T^5$ is H. In another embodiment, $T^5$ is $Q^1$. In another embodiment, $T^5$ is $OQ^1$. In another embodiment, $T^5$ is $CF_3$. In another embodiment, $T^5$ is $C(O)Q^1$. In another embodiment, $T^5$ is $COOQ^1$. In another embodiment, $T^5$ is $CON(Q^1)_2$. In another embodiment, $T^5$ is $NQ^1Q^2$. In another embodiment, $T^5$ is $NO_2$. In another embodiment, $T^5$ is CN. In another embodiment, $T^5$ is $SO_3^-$. In another embodiment, $T^5$ is $SO_3M$. In another embodiment, $T^5$ is $SO_3H$. In another embodiment, $T^5$ is $SQ^1$. In another embodiment, $T^5$ is —$NQ^1Q^2CONQ^3Q^4$. In another embodiment, $T^5$ is NCO. In another embodiment, $T^5$ is NCS. In another embodiment, $T^5$ is alkenyl. In another embodiment, $T^5$ is alkynyl. In another embodiment, $T^5$ is epoxide. In another embodiment, $T^5$ is alkylated epoxide. In another embodiment, $T^5$ is azide. In another embodiment, $T^5$ is halide.

In one embodiment, $T^{5'}$ of formula VII-IX is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $T^{5'}$ is H. In another embodiment, $T^{5'}$ is $Q^1$. In another embodiment, $T^{5'}$ is $OQ^1$. In another embodiment, $T^{5'}$ is $CF_3$. In another embodiment, $T^{5'}$ is $C(O)Q^1$. In another embodiment, $T^{5'}$ is $COOQ^1$. In another embodiment, $T^{5'}$ is $CON(Q^1)_2$. In another embodiment, $T^{5'}$ is $NQ^1Q^2$. In another embodiment, $T^{5'}$ is $NO_2$. In another embodiment, $T^{5'}$ is CN. In another embodiment, $T^{5'}$ is $SO_3$. In another embodiment, $T^{5'}$ is $SO_3M$. In another embodiment, $T^{5'}$ is $SO_3H$. In another embodiment, $T^{5'}$ is $SQ^1$. In another embodiment, $T^{5'}$ is, —$NQ^1Q^2CONQ^3Q^4$. In another embodiment, $T^{5'}$ is NCO. In another embodiment, $T^{5'}$ is NCS. In another embodiment, $T^{5'}$ is alkenyl. In another embodiment, $T^{5'}$ is alkynyl. In another embodiment, $T^{5'}$ is epoxide. In another embodiment, $T^{5'}$ is alkylated epoxide. In another embodiment, $T^{5'}$ is azide. In another embodiment, $T^{5'}$ is halide.

In one embodiment, $T^6$ of formula VII-VIII is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $T^6$ is H. In another embodiment, $T^6$ is $Q^1$. In another embodiment, $T^6$ is $OQ^1$. In another embodiment, $T^6$ is $CF_3$. In another embodiment, $T^6$ is $C(O)Q^1$. In another embodiment, $T^6$ is $COOQ^1$. In another embodiment, $T^6$ is $CON(Q^1)_2$. In another embodiment, $T^6$ is $NQ^1Q^2$. In another embodiment, $T^6$ is $NO_2$. In another embodiment, $T^6$ is CN. In another embodiment, $T^6$ is $SO_3^-$. In another embodiment, $T^6$ is $SO_3M$. In another embodiment, $T^6$ is $SO_3H$. In another embodiment, $T^6$ is $SQ^1$. In another embodiment, $T^6$ is, —$NQ^1Q^2CONQ^3Q^4$. In another embodiment, $T^6$ is NCO. In another embodiment, $T^6$ is NCS. In another embodiment, $T^6$ is alkenyl. In another embodiment, $T^6$ is alkynyl. In another embodiment, $T^6$ is epoxide. In another embodiment, $T^6$ is alkylated epoxide. In another embodiment, $T^6$ is azide. In another embodiment, $T^6$ is halide.

In one embodiment, $T^{6'}$ of formula VII-VIII is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $T^{6'}$ is H. In another embodiment, $T^{6'}$ is $Q^1$. In another embodiment, $T^{6'}$ is $OQ^1$. In another embodiment, $T^{6'}$ is $CF_3$. In another embodiment, $T^{6'}$ is $C(O)Q^1$. In another embodiment, $T^{6'}$ is $COOQ^1$. In another embodiment, $T^{6'}$ is $CON(Q^1)_2$. In another embodiment, $T^{6'}$ is $NQ^1Q^2$. In another embodiment, $T^{6'}$ is $NO_2$. In another embodiment, $T^{6'}$ is CN. In another embodiment, $T^{6'}$ is $SO_3^-$. In another embodiment, $T^{6'}$ is $SO_3M$. In another embodiment, $T^{6'}$ is $SO_3H$. In another embodiment, $T^{6'}$ is $SQ^1$. In another embodiment, $T^6$ is, —$NQ^1Q^2CONQ^3Q^4$. In another embodiment, $T^{6'}$ is NCO. In another embodiment, $T^{6'}$ is NCS. In another embodiment, $T^{6'}$ is alkenyl. In another embodiment, $T^{6'}$ is alkynyl. In another embodiment, $T^{6'}$ is epoxide. In another embodiment, $T^{6'}$ is alkylated epoxide. In another embodiment, $T^{6'}$ is azide. In another embodiment, $T^{6'}$ is halide.

In one embodiment, $T^7$ of formula VII is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $T^7$ is H. In another embodiment, $T^7$ is $Q^1$. In another embodiment, $T^7$ is $OQ^1$. In another embodiment, $T^7$ is $CF_3$. In another embodiment, $T^7$ is $C(O)Q^1$. In another embodiment, $T^7$ is $COOQ^1$. In another embodiment, $T^7$ is $CON(Q^1)_2$. In another embodiment, $T^7$ is $NQ^1Q^2$. In another embodiment, $T^7$ is $NO_2$. In another embodiment, $T^7$ is CN. In another embodiment, $T^7$ is $SO_3^-$. In another embodiment, $T^7$ is $SO_3M$. In another embodiment, $T^7$ is $SO_3H$. In another embodiment, $T^7$ is $SQ^1$. In another embodiment, $T^7$ is, —$NQ^1Q^2CONQ^3Q^4$. In another embodiment, $T^7$ is NCO. In another embodiment, $T^7$ is NCS. In another embodiment, $T^7$ is alkenyl. In another embodiment, $T^7$ is alkynyl. In another embodiment, $T^7$ is epoxide. In another embodiment, $T^7$ is alkylated epoxide. In another embodiment, $T^7$ is azide. In another embodiment, $T^7$ is halide.

In one embodiment, $T^{7'}$ of formula VII is H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, —$NQ^1Q^2CONQ^3Q^4$, NCO, NCS, alkenyl, alkynyl, epoxide, alkylated epoxide, azide or halide. In another embodiment, $T^{7'}$ is H. In another embodiment, $T^{7'}$ is $Q^1$. In another embodiment, $T^{7'}$ is $OQ^1$. In another embodiment, $T^{7'}$ is $CF_3$. In another embodiment, $T^{7'}$ is $C(O)Q^1$. In another embodiment, $T^{7'}$ is $COOQ^1$. In another embodiment, $T^{7'}$ is $CON(Q^1)_2$. In another embodiment, $T^{7'}$ is $NQ^1Q^2$. In another embodiment, $T^{7'}$ is $NO_2$. In another embodiment, $T^{7'}$ is CN. In another embodiment, $T^{7'}$ is $SO_3^-$. In another embodiment, $T^{7'}$ is $SO_3M$. In another embodiment, $T^{7'}$ is $SO_3H$. In another embodiment, $T^{7'}$ is $SQ^1$. In another embodiment, $T^{7'}$ is, —$NQ^1Q^2CONQ^3Q^4$. In another embodiment, $T^{7'}$ is NCO. In another embodiment, $T^{7'}$ is NCS. In another embodiment, $T^{7'}$ is alkenyl. In another embodiment, $T^{7'}$ is alkynyl. In another embodiment, $T^{7'}$ is epoxide. In another embodiment, $T^{7'}$ is alkylated epoxide. In another embodiment, $T^{7'}$ is azide. In another embodiment, $T^{7'}$ is halide.

In one embodiment, $T^4$ and $T^5$ form together a N-heterocyclic ring wherein said ring is optionally substituted. In another embodiment, the N-heterocyclic ring is substituted by one or more groups selected from halide, hydroxy, alkoxy, carboxylic acid, aldehyde, carbonyl, amido, cyano, nitro, amino, alkenyl, alkynyl, aryl, azide, epoxide, ester, acyl chloride and thiol.

In one embodiment, the alkyl of formula I-X is optionally substituted linear, branched, cyclic or heterocyclic. In another embodiment, alkyl is linear or branched. In another embodiment, alkyl is optionally substituted linear alkyl. In another embodiment, alkyl is optionally substituted branched alkyl.

An "alkyl" group refers, in one embodiment, to a saturated aliphatic hydrocarbon, including straight-chain or branched-chain. In one embodiment, the alkyl group has 1-20 carbons. In another embodiment, the alkyl group has 1-8 carbons. In another embodiment, the alkyl group has 1-7 carbons. In another embodiment, the alkyl group has 1-6 carbons. Non limiting examples of alkyl groups include methyl, ethyl, propyl, isobutyl, butyl, pentyl or hexyl. In another embodiment, the alkyl group has 1-4 carbons. In another embodiment, the alkyl group may be optionally substituted by one or more groups selected from halide, hydroxy, alkoxy, carboxylic acid, aldehyde, carbonyl, amido, cyano, nitro, amino, alkenyl, alkynyl, aryl, azide, epoxide, ester, acyl chloride and thiol.

A "cycloalkyl" group refers, in one embodiment, to a ring structure comprising carbon atoms as ring atoms, which are saturated, substituted or unsubstituted. In another embodiment the cycloalkyl is a 3-12 membered ring. In another embodiment the cycloalkyl is a 6 membered ring. In another embodiment the cycloalkyl is a 5-7 membered ring. In another embodiment the cycloalkyl is a 3-8 membered ring. In another embodiment, the cycloalkyl group may be unsubstituted or substituted by a halide, alkyl, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the cycloalkyl ring may be fused to another saturated or unsaturated 3-8 membered ring. In another embodiment, the cycloalkyl ring is an unsaturated ring. Non limiting examples of a cycloalkyl group comprise cyclohexyl, cyclohexenyl, cyclopropyl, cyclopropenyl, cyclopentyl, cyclopentenyl, cyclobutyl, cyclobutenyl, cyclooctyl, cyclooctadienyl (COD), cyclooctaene (COE) etc.

A "heterocycloalkyl" group refers in one embodiment, to a ring structure of a cycloalkyl as described herein comprising in addition to carbon atoms, sulfur, oxygen, nitrogen or any combination thereof, as part of the ring. In one embodiment, non-limiting examples of heterocycloalkyl of formula I-X include pyrrolidine, pyrrole, tetrahydrofuran, furan, thiolane, thiophene, imidazole, pyrazole, pyrazolidine, oxazolidine, oxazole, isoxazole, thiazole, isothiazole, thiazolidine, dioxolane, dithiolane, triazole, furazan, oxadiazole, thiadiazole, dithiazole, tetrazole, piperidine, oxane, thiane, pyridine, pyran, thiopyran, piperazine, morpholine, thiomorpholine, dioxane, dithiane, diazine, oxazine, thiazine, dioxine, triazine, and trioxane.

As used herein, the term "aryl" refers to any aromatic ring that is directly bonded to another group and can be either substituted or unsubstituted. The aryl group can be a sole substituent, or the aryl group can be a component of a larger substituent, such as in an arylalkyl, arylamino, arylamido, etc. Exemplary aryl groups include, without limitation, phenyl, tolyl, xylyl, furanyl, naphthyl, pyridinyl, pyrimidinyl, pyridazinyl, pyrazinyl, triazinyl, thiazolyl, oxazolyl, isooxazolyl, pyrazolyl, imidazolyl, thiophene-yl, pyrrolyl, phenylmethyl, phenylethyl, phenylamino, phenylamido, etc. Substitutions include but are not limited to: F, Cl, Br, I, $C_1$-$C_5$ linear or branched alkyl, $C_1$-$C_5$ linear or branched haloalkyl, $C_1$-$C_5$ linear or branched alkoxy, $C_1$-$C_5$ linear or branched haloalkoxy, aryl, heterocycloalkyl, $CF_3$, CN, $NO_2$, —$CH_2CN$, $NH_2$, NH-alkyl, N(alkyl)$_2$, hydroxyl, —OC(O)$CF_3$, —OCH$_2$Ph, —NHCO-alkyl, COOH, —C(O)Ph, C(O)O-alkyl, C(O)H, or - or —C(O)NH$_2$.

In one embodiment, the term "halide" used herein refers to any substituent of the halogen group (group 17). In another embodiment, halide is flouride, chloride, bromide or iodide. In another embodiment, halide is fluoride. In another embodiment, halide is chloride. In another embodiment, halide is bromide. In another embodiment, halide is iodide.

In one embodiment, haloalkyl of formula I-X refers to alkyl, or cycloalkyl substituted with one or more halide atoms. In another embodiment haloalkyl is perhalogenated (completely halogenated, no C—H bonds). In another embodiment, haloalkyl is $CH_2CF_3$. In another embodiment. haloalkyl is $CH_2CCl_3$. In another embodiment, haloalkyl is $CH_2CBr_3$. In another embodiment, haloalkyl is $CH_2Cl_3$. In another embodiment, haloalkyl is $CF_2CF_3$. In another embodiment, haloalkyl is $CH_2CH_2CF_3$. In another embodiment, haloalkyl is $CH_2CF_2CF_3$. In another embodiment, haloalkyl is $CF_2CF_2CF_3$.

In one embodiment, M of formula I-X is a monovalent cation. In another embodiment, non-limiting examples of M include alkali metal cations, $NH_4^+$, $N(Q^3)_4^+$, and $P(Q^3)_4^+$. In another embodiment, M is $Li^+$ In another embodiment, M is $Na^+$ In another embodiment, M is $K^+$. In another embodiment, M is $Rb^+$. In another embodiment, M is $Cs^+$. In another embodiment, non-limiting examples of the quarternary ammonium cation, $N(Q^3)_4^+$, include tetrametylammonium, tetraethylammonium, tetrabutylammonium, tetraoctylammonium, trimethyloctylammonium and cetyltrimethylammonium. In another embodiment, non-limiting examples of the quarternary phosphonium cation, $P(Q^3)_4^+$, include tetraphenylphosphonium, dimethyldiphenylphosphonium, tetrabutylphosphonium, methyltriphenoxyphosphonium and tetramethylphosphonium.

In one embodiment, the term "alkenyl" used herein refers to any alkyl group wherein at least one carbon-carbon double bond (C═C) is found. In another embodiment, the carbon-carbon double bond is found in one terminal of the alkenyl group. In another embodiment, the carbon-carbon double bond is found in the middle of the alkenyl group. In another embodiment, more than one carbon-carbon double bond is found in the alkenyl group. In another embodiment, three carbon-carbon double bonds are found in the alkenyl group. In another embodiment, four carbon-carbon double bonds are found in the alkenyl group. In another embodiment, five carbon-carbon double bonds are found in the alkenyl group. In another embodiment, the alkenyl group comprises a conjugated system of adjacent alternating single and double carbon-carbon bonds. In another embodiment, the alkenyl group is a cycloalkenyl, wherein "cycloalkenyl" refers to a cycloalkyl comprising at least one double bond.

In one embodiment, the term "alkynyl" used herein refers to any alkyl group wherein at least one carbon-carbon triple bond (C≡C) is found. In another embodiment, the carbon-carbon triple bond is found in one terminal of the alkynyl group. In another embodiment, the carbon-carbon triple bond is found in the middle of the alkynyl group. In another embodiment, more than one carbon-carbon triple bond is found in the alkynyl group. In another embodiment, three carbon-carbon triple bonds are found in the alkynyl group. In another embodiment, four carbon-carbon triple bonds are found in the alkynyl group. In another embodiment, five carbon-carbon triple bonds are found in the alkynyl group. In another embodiment, the alkynyl group comprises a conjugated system. In another embodiment, the conjugated system is of adjacent alternating single and triple carbon-carbon bonds. In another embodiment, the conjugated system is of adjacent alternating double and triple carbon-carbon bonds. In another embodiment, the alkynyl group is a cycloalkynyl, wherein "cycloalkynyl" refers to a cycloalkyl comprising at least one triple bond.

In one embodiment, the term "alkylated epoxide" used herein refers to any alkylated substituent comprising an epoxide group (a 3 membered ring consisting of oxygen and two carbon atoms). In another embodiment, the epoxide group is in the middle of the alkyl. In another embodiment, the epoxide group is in one terminal of the alkyl. In another embodiment, the alkyl is a cycloalkyl. In another embodiment, the alkyl is an alkenyl. In another embodiment, the alkyl is an alkynyl. In another embodiment, the epoxide is monoalkylated. In another embodiment, the epoxide is dialkylated. In another embodiment, the epoxide is trialkylated. In another embodiment, the epoxide is tetraalkylated.

In one embodiment, this invention is directed to a photoluminescent compound represented by the structure of formula 8, 9, 10, 11, 12, 15 or 16:

8

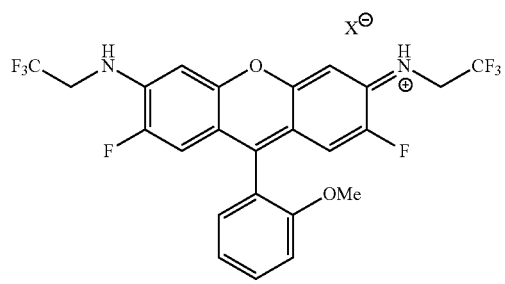

9

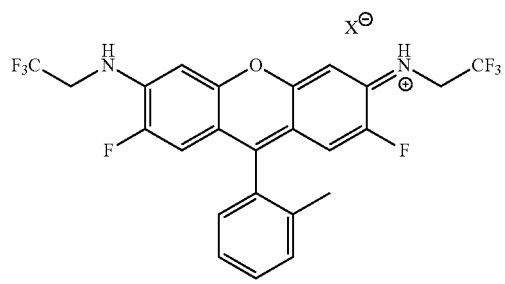

10

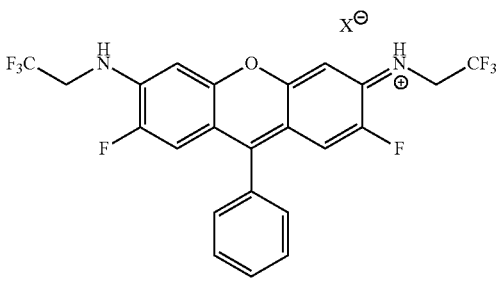

11

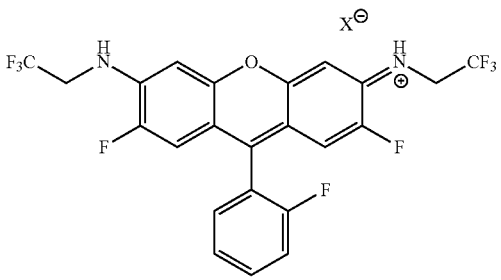

12

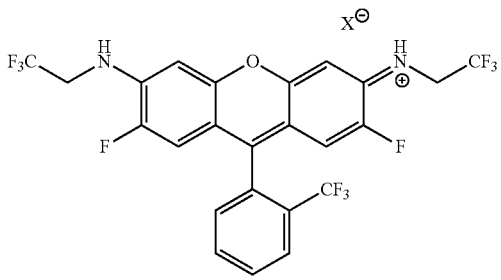

15

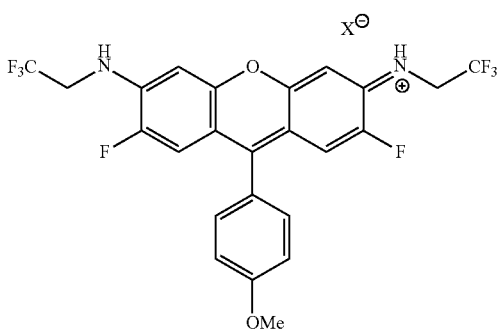

16

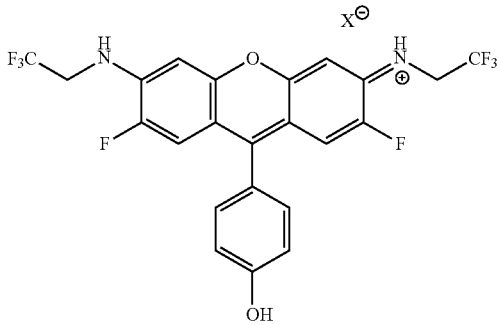

In one embodiment, X of compounds of formula I-X, 8-12 and 15-16 is an anion. In another embodiment, the anion is a monovalent. In another embodiment the anion is polyvalent. In another embodiment the anion is a sulfate, chloride, bromide, iodide, perchlorate, nitrate, trifluoroacetate, hydroxide, hydrosulfide, sulfide, nitrite, carboxylate, dicarboxylate, sulfonate, tetraflouroborate hexaflourophosphate, hypophosphite, phosphate, phosphite, cyanate, cyanide, isocyanate, thiocyanate, tetralkylborate, tetraarylborate or chromate. In another embodiment, non-limiting groups of carboxylate include formate, propionate, butyrate, lactate, pyruvate, tartrate, ascorbate, gluconate, glutamate, citrate, succinate, maleate, 4-pyridinecarboxylate, 2-hydroxypropanoate and glucoronate. In another embodiments, non-limiting groups of sulfonate include mesylate, tosylate, ethanesulfonate, benzenesulfonate, and triflate. In another embodiment, non-limiting groups of tetraalkylborates include tetramethylborate, trimethylethylborate and triethylbutylborate. In another embodiment, non-limiting groups of tetraaryylborates include tetrakis[3,5-bis(trifluoromethyl)phenyl]borate, tetrakis(4-chlorophenyl)borate, tetrakis(pentaflourophenyl)borate and tetrakis(4-fluorophenyl)borate.

In one embodiment, the photoluminescent compounds of this invention emit in ethanol solution at a wavelength of between 520 nm to 560 nm. In another embodiment, the photoluminescent material of compound of formula 8 emits at 527 nm in ethanol. In another embodiment, the photoluminescent material of compound of formula 9 emits at 525 nm in ethanol. In another embodiment, the photoluminescent material of compound of formula 10 emits at 525 nm in ethanol. In another embodiment, the photoluminescent material of compound of formula 11 emits at 538 nm in ethanol. In another embodiment, the photoluminescent material of compound of formula 12 emits at 533 nm in ethanol. In another embodiment, the photoluminescent material of compound of formula 15 emits at 525 nm in ethanol. In another embodiment, the photoluminescent material of compound of formula 16 emits at 523 nm in ethanol.

In one embodiment, the photoluminescent compounds of this invention possess a sharp emission peak with small FWHM (Full Width at Half Maximum) values between 30-55 nm. In another embodiment, the photoluminescent material of compound of formula 8 has FWHM of 32 nm for the emission peak. In another embodiment, the photoluminescent material of compound of formula 9 has FWHM of 32 nm for the emission peak. In another embodiment, the photoluminescent material of compound of formula 10 has FWHM of 35 nm for the emission peak. In another embodiment, the photoluminescent material of compound of formula 11 has FWHM of 41 nm for the emission peak. In another embodiment, the photoluminescent material of compound of formula 12 has FWHM of 34 nm for the emission peak. In another embodiment, the photoluminescent material of compound of formula 15 has FWHM of 35 nm for the emission peak. In another embodiment, the photoluminescent material of compound of formula 16 has FWHM of 41 nm for the emission peak.

OLEDs (organic light emitting diodes) have attracted much attention for application to next-generation displays. During the past decade, several commercial products have been developed using small OLEDs fabricated by vacuum evaporation. However, current OLED technology still have limited color gamut. Therefore, it is required to continue develop alternative technologies, such as LCD with the proposed innovation.

White-light emitting diodes based on blue inorganic emitters (InGaN based) coated with phosphor materials are regularly used. The semiconductor device converts its original blue radiation into a yellow-green light (by the phosphor based compound) that, combined with the remaining blue light from the irradiation source, yields an overall white-yellowish emission. This white-yellowish emission from such device does not yield a good quality white emission, since besides the good blue emission from the InGaN LED, the remaining yellowish emission has a broad FWHM (Full Width at Half Maximum), resulting in narrow color gamut. Alternative fluorescent inorganic compounds used are quantum dots but they do not offer either the efficiency, durability, or the competitive cost demanded by the display devices. Moreover, quantum dots are based mostly on toxic cadmium compounds while there is a worldwide legislation ((US EPA TSCA—Toxic Substances Control Act) and European Regulation of hazardous Substances (RoHS)) soon to become effective that forbids the use of such materials.

In Liquid Crystal Displays (LCDs) the image is created by combining three basic colors—Red, Green and Blue at different ratios. Each ratio combination provides one color out of all possible colors of the display, which altogether define the Color Gamut of the display. There are three main components responsible for controlling the color production—the backlight unit which generates the basic color (White), the LCD which is a matrix of pixels each controlling the amount of color passing through, and the color filters that filter out each sub-pixel to leave only its required color (Red, Green or Blue). Two parameters that impacts the Color Gamut coverage are (1) the color spectra peak wavelength and (2) FWHM for each color wavelengths. As the blue, green and red peaks are near ~450, ~530 and above 620 nm, respectively and also that each peak has a narrower FWHM results in obtaining a larger the Color Gamut, or in other words more colors can be produced. To increase the color gamut of a display, in relevance to the maximum human eye color saturation, the light source needs to have narrow bands (FWHM) at the corresponding blue, green and red color wavelengths mentioned above (~450, ~530 and above 620 nm up to 700 nm), respectively and also that each peak has a narrower FWHM results in obtaining a larger the Color Gamut, or in other words more colors can be produced.

Other solution could have been using three different LEDs each emitting at the red, green and blue, respectively. However, the cost and complexity of this solution made this option non economical for most display applications.

In order to circumvent the lighting quality and the color rendering issues, organic fluorescent dyes have been developed, which give access to both a large number of available molecules and to the possibility of easily tuning their emission spectra by molecular engineering. Fluorescent molecular dyes such as perylene and naphthalene based derivatives, for instance, have been synthesized as highly efficient and highly stable fluorescent molecules. Despite their promising emission properties, such organic dyes often suffer from a lack of the required long-term thermal and chemical photo-stability when submitted to the severe physical-chemical conditions encountered in most lighting devices. In order to increase the photostability, modified fluorophores have been developed by combining the photoluminescent (PL) compounds in solid matrices. Such solid matrices can be produced in either (1) film form above the direct Backlight Unit (BLU) or waveguide, (2) glass/plastic tubes in close proximity to the LEDs in the BLU. Moreover, the embedment can further enhance the PL properties, such as narrower FWHM and enabling polarized emission. Examples of solid matrices include: epoxies, poly-acrylates, silicon resins, polyethylene glycols based polymers, liquid crystals, modified glass based on sol-gel methodology, or combination thereof (such as mixing sol-gel matrix and all is encapsulated in an additional epoxy matrix).

In one embodiment, this invention is directed to produce color-conversion-layer that is integrated in a display device, and more particularly, to a photoluminescent LCD comprising a compound of formula I-X or combination thereof. In another embodiment, the LCD comprises a compound of formula 8. In another embodiment, the LCD comprises a compound of formula 9. In another embodiment, the LCD comprises a compound of formula 10. In another embodiment, the LCD comprises a compound of formula 11. In another embodiment, the LCD comprises a compound of formula 12. In another embodiment, the LCD comprises a compound of formula 15. In another embodiment, the LCD comprises a compound of formula 16. In another embodiment, the LCD comprises a compound of formula 8, 9, 10, 11, 12, 15, 16 or combination thereof.

In one embodiment, the photoluminescent LCD comprises a display panel that displays red, green and blue sub-pixel areas, an excitation source operable to generate excitation radiation for operating the display and a color-elements plate. The color-elements plate comprises a film comprising at least one photoluminescent compound of this invention that is operable to emit a light corresponding to red, green or blue pixel areas of the display, in response to said excitation radiation. In another embodiment, the photoluminescent compounds of this emits light between 520 nm to 560 nm and is embedded in a solid matrix film in the LCD, yielding higher brightness and color gamut compared to typical white LED based device solutions.

In one embodiment, the photoluminescent LCD comprises: a display panel comprising light transmissive front and back plates; an excitation source operable to generate excitation radiation for operating the display; a liquid crystal disposed between the front and back plates; a matrix of electrodes defining red, green and blue pixel areas of the display and operable to selectively induce an electric field across the liquid crystal in the pixel areas for controlling transmission of light through the pixels areas; and a photoluminescence color-elements plate, wherein the color-element plate comprises at least one of the photoluminescent compounds of this invention. In another embodiment, the compound is a compound of formula I-VI. In another embodiment, the LCD comprises a compound of formula 8. In another embodiment, the LCD comprises a compound of formula 9. In another embodiment, the LCD comprises a compound of formula 10. In another embodiment, the LCD comprises a compound of formula 11. In another embodiment, the LCD comprises a compound of formula 12. In another embodiment, the LCD comprises a compound of formula 15. In another embodiment, the LCD comprises a compound of formula 16.

In yet another aspect the invention provides a liquid crystal display wherein the compound of this invention is embedded in a solid matrix. Non limiting examples of solid matrices include: epoxides, poly-acrylates, silicon resins, polyethylene glycols based polymers, liquid crystals, modified glass based on sol-gel methodology, or combination thereof.

In one embodiment, this invention provides a photoluminescent device comprising: a transparent, semi-transparent or diffusing substrate encapsulating or coated with a photoluminescent compound of this invention. In another embodiment, the photoluminescent device is integrated in a LCD display.

In some embodiments, the compounds of the invention are used as bio-markers, medical markers, in photovoltaic cells, in solar cells, sensors, as electroluminescent materials, as laser dyes, theranostics, molecular probes for scientific research, ink for printing, exterior lighting applications, signage, cosmetics, or as dyes. In another embodiment, the compounds are used as dyes wherein the dyes are applied in glow sticks ("stick-lights").

The following examples are presented in order to more fully illustrate the preferred embodiments of the invention. They should in no way, however, be construed as limiting the broad scope of the invention.

EXAMPLES

Synthesis of Compounds 1 and 2

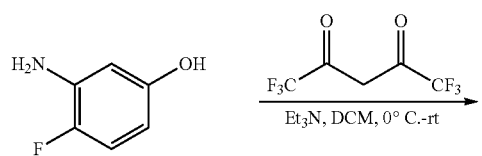

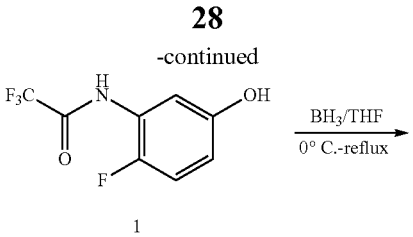

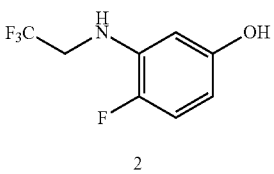

Example 1

Synthesis of 2,2,2-trifluoro-N-(2-fluoro-5-hydroxyphenyl)acetamide (1)

To a stirred solution of 3-amino-4-fluorophenol (2.0 gr, 15.7 mmol) and trimethylamine (8.8 ml, 62.8 mmol) in DCM (52 ml), trifluoroacetic anhydride (2.6 ml, 18.8 mmol) in DCM (8 ml) was added dropwise at 0° C. The reaction was stirred overnight at room temperature. After reaction completion the mixture was diluted with H$_2$O (50 ml), the organic layer was separated and washed with HCl (1N, 50 ml), water (50 ml) and brine (50 ml). The organic solution was dried over MgSO$_4$ and concentrated under reduced pressure to yield a white solid 1 (3.4 gr, 98%).

$^1$H NMR (CD$_3$OD-d4, 400 MHz): δ 7.07 (dd, J=6.0 Hz, J=2.8 Hz, 1H), 7.02 (dd, J=10.4 Hz, J=9.2 Hz, 1H), 6.70 (ddd, J=9.2 Hz, J=4.0 Hz, J=3.2 Hz, 1H).

Synthesis of 4-fluoro-3-((2,2,2-trifluoroethyl)amino)phenol (2)

To a stirred solution of 1 (3.4 gr, 15.2 mmol) in THF (40 ml), 1 M solution of BH$_3$ in THF (52 0.2 mL) was added at 0° C. and the reaction mixture was refluxed overnight. After reaction completion, MeOH (8 ml), followed by 1N NaOH (32 ml) were added at 0° C. After stirring at room temperature for 20 min, the mixture was diluted with ether (120 ml), and the organic layer was separated. The aqueous layer was extracted with ether (3×60 ml). Combined organic solutions were washed with sat. aq. NaHCO$_3$ (150 ml), brine (150 ml), dried over MgSO$_4$ and concentrated under reduced pressure. Purification by flash column chromatography (SiO$_2$, EtOAc: Hex) afforded the pure product 2 as a white solid (3.0 g, 95%). $^1$H NMR (CDCl$_3$, 400 MHz): δ 6.76 (dd, J=11.6 Hz, J=8.7 Hz, 1H), 6.28 (dd, J=7.4 Hz, J=2.8 Hz, 1H), 6.05 (ddd, J=8.7 Hz, J=3.5 Hz, J=2.9 Hz, 1H), 3.80 (q, J=9.3 Hz, 2H).

Example 2

Synthesis of 6,6'-((2-methoxyphenyl)methylene)bis(4-fluoro-3-((2,2,2-trifluoroethyl)amino)phenol) (3)

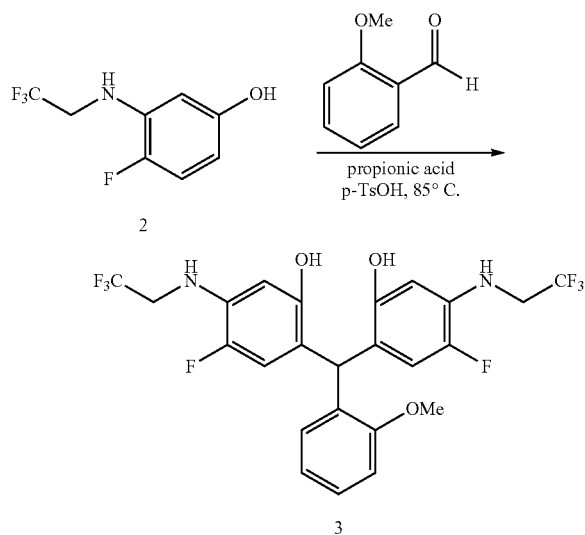

This process is based on B. R. Peterson et al. (*Beilstein J. Org. Chem.* 2012, 8, 2156-2165). Compound 2 (0.3 gr, 1.4 mmol) was dissolved in propionic acid (15 ml). Then o-anisaldehyde (0.098 gr, 0.72 mmol) and catalytic p-TsOH were added at room temperature, and the reaction was heated to 80-85° C. for 20 h. After reaction completion, the solution was cooled to 0° C., poured into excess of aqueous sodium acetate solution (3 M, 50 ml) and extracted with ethyl acetate (75 ml). The organic layer was washed twice with water (50 ml), dried over MgSO$_4$ and concentrated under reduced pressure. Purification by flash column chromatography (SiO$_2$, EtOAc:Hex) afforded the pure product 3 as a brown solid (0.34 g, 89%). $^1$H NMR (CDCl$_3$, 400 MHz, ppm): δ 7.30-7.27 (m, 1H), 6.97-6.91 (m, 3H), 6.50 (d, J=12.4 Hz, 2H), 6.51 (d, J=7.6 Hz, 2H), 5.83 (s, 1H), 3.78 (s, 3H), 3.73 (q, J=8.8 Hz, 4H).

Example 3

Synthesis of 6,6'-((2-methoxyphenyl)methylene)bis(4-fluoro-3-((2,2,2-trifluoroethyl)amino)phenol) (4)

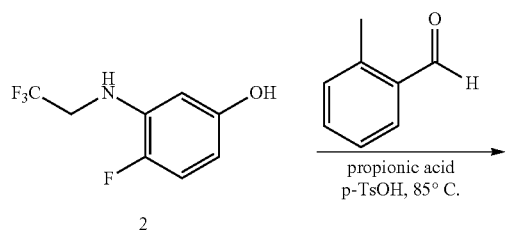

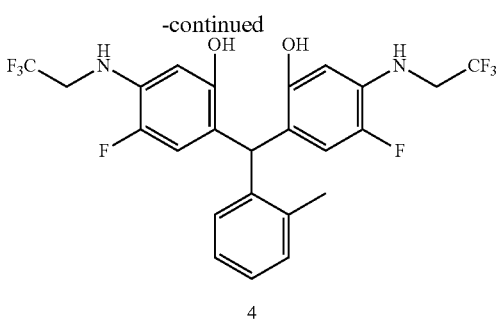

This process is based on B. R. Peterson et al. (*Beilstein J. Org. Chem.* 2012, 8, 2156-2165). Compound 2 (0.3 gr, 1.4 mmol) was dissolved in propionic acid (15 ml). Then o-tolualdehyde (0.085 ml, 0.72 mmol) and catalytic p-TsOH were added at room temperature, and the reaction was heated to 80-85° C. for 20 h. After reaction completion, the solution was cooled to 0° C., poured into excess of aqueous sodium acetate solution (3 M, 50 ml) and extracted with ethyl acetate (75 ml). The organic layer was washed twice with water (50 ml), dried over MgSO$_4$ and concentrated under reduced pressure. Purification by flash column chromatography (SiO$_2$, EtOAc:Hex) afforded the pure product 4 as a brown solid (0.35 gr, 93%).
$^1$H NMR (CDCl$_3$, 400 MHz): δ 7.21-7.12 (m, 3H), 6.89 (m, 1H), 6.39 (d, J=12.4 Hz, 2H), 6.30 (d, J=7.6 Hz, 2H), 5.67 (s, 1H), 3.74 (q, J=8.8 Hz, 4H), 2.20 (s, 3H).

Example 4

Synthesis of 6,6'-(phenylmethylene)bis(4-fluoro-3-((2,2,2-trifluoroethyl)amino)phenol) (5)

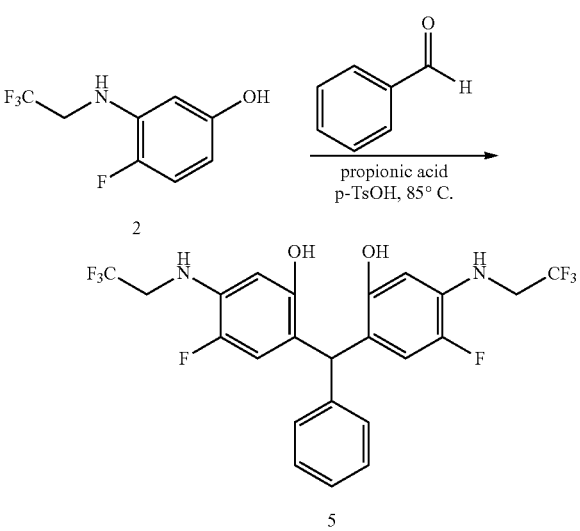

This process is based on B. R. Peterson et al. (*Beilstein J. Org. Chem.* 2012, 8, 2156-2165). Compound 2 (0.3 gr, 1.4 mmol) was dissolved in propionic acid (15 ml). Then benzaldehyde (0.073 ml, 0.72 mmol) and catalytic p-TsOH were added at room temperature, and the reaction was heated to 80-85° C. for 20 h. After reaction completion, the solution was cooled to 0° C., poured into excess of aqueous sodium acetate solution (3 M, 50 ml) and extracted with ethyl acetate (75 ml). The organic layer was washed twice with water (50 ml), dried over MgSO₄ and concentrated under reduced pressure. Purification by flash column chromatography (SiO₂, EtOAc:Hex) afforded the pure product 5 as a brown solid (0.26 gr, 73%).

¹H NMR (CDCl₃, 400 MHz): δ 7.35-7.25 (m, 3H), 7.15-7.13 (m, 2H), 6.50 (d, J=12.4 Hz, 2H), 6.28 (d, J=7.6 Hz, 2H), 5.65 (s, 1H), 3.71 (q, J=8.8 Hz, 4H).

Example 5

Synthesis of 6,6'-((2-fluorophenyl)methylene)bis(4-fluoro-3-((2,2,2-trifluoroethyl)amino)phenol) (6)

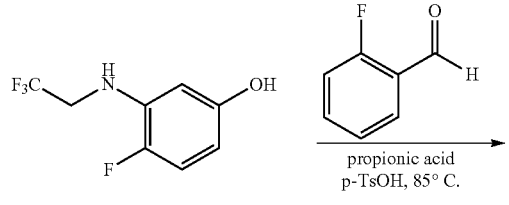

2

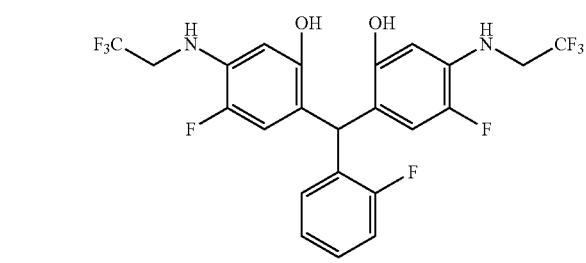

6

This process is based on B. R. Peterson et al. (*Beilstein J. Org. Chem.* 2012, 8, 2156-2165). Compound 2 (0.3 gr, 1.4 mmol) was dissolved in propionic acid (15 ml). Then fluorobenzaldehyde (0.075 ml, 0.72 mmol) and catalytic p-TsOH were added at room temperature, and the reaction was heated to 80-85° C. for 20 h. After reaction completion, the solution was cooled to 0° C., poured into excess of aqueous sodium acetate solution (3 M, 50 ml) and extracted with ethyl acetate (75 ml). The organic layer was washed twice with water (50 ml), dried over MgSO₄ and concentrated under reduced pressure. Purification by flash column chromatography (SiO₂, EtOAc:Hex) afforded the pure product 6 as a brown solid (0.15 gr, 40%).

¹H NMR (CDCl₃, 400 MHz): δ 7.11-6.94 (m, 4H), 6.47 (d, J=12.0 Hz, 2H), 6.29 (d, J=7.6 Hz, 2H), 5.89 (s, 1H), 3.74 (q, J=7.6 Hz, 4H).

Example 6

Synthesis of 6,6'-((2-fluorophenyl)methylene)bis(4-fluoro-3-((2,2,2-trifluoroethyl)amino)phenol) (7)

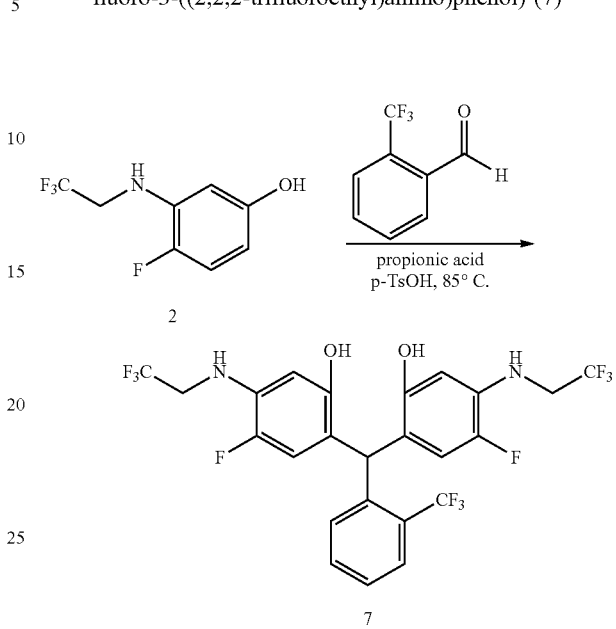

7

This process is based on B. R. Peterson et al. (*Beilstein J. Org. Chem.* 2012, 8, 2156-2165). Compound 2 (0.3 gr, 1.4 mmol) was dissolved in propionic acid (15 ml). Then o-(trifluoromethyl)benzaldehyde (0.095 ml, 0.72 mmol) and catalytic p-TsOH were added at room temperature, and the reaction was heated to 80-85° C. for 20 h. After reaction completion, the solution was cooled to 0° C., poured into excess of aqueous sodium acetate solution (3 M, 50 ml) and extracted with ethyl acetate (75 ml). The organic layer was washed twice with water (50 ml), dried over MgSO₄ and concentrated under reduced pressure. Purification by flash column chromatography (SiO₂, EtOAc:Hex) afforded the pure product as a brown solid (0.33 gr, 79%). ¹H NMR (CDCl₃, 400 MHz, ppm): δ 7.72 (d, J=7.6 Hz, 1H), 7.52-7.37 (m, 2H), 7.19-716 (m, 1H), 6.37 (d, J=12.3 Hz, 2H), 6.27 (d, J=7.5 Hz, 2H), 6.01 (s, 1H), 3.78-3.71 (m, 4H).

Example 7

Synthesis of 6,6'-((4-methoxyphenyl)methylene)bis(4-fluoro-3-((2,2,2-trifluoroethyl)amino)phenol) (13)

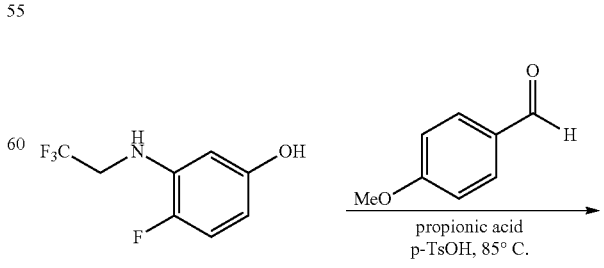

2

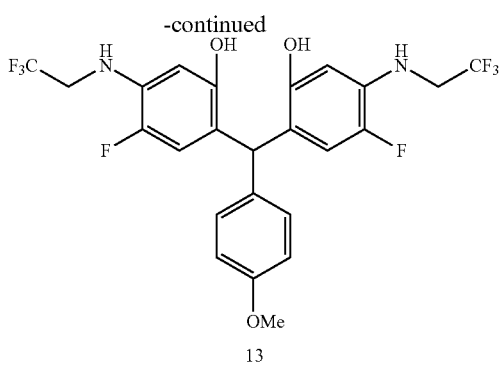

13

This process is based on B. R. Peterson et al. (*Beilstein J. Org. Chem.* 2012, 8, 2156-2165). Compound 2 (0.4 gr, 1.9 mmol) was dissolved in propionic acid (10 ml). Then 4-methoxybenzaldehyde (0.12 ml, 0.96 mmol) and catalytic p-TsOH were added at room temperature, and the reaction was heated to 80-85° C. for 5 h. After reaction completion, the solution was cooled to 0° C., poured into excess of aqueous sodium acetate solution (3 M, 40 ml) and extracted with ethyl acetate (60 ml). The organic layer was washed twice with water (40 ml), dried over MgSO$_4$ and concentrated under reduced pressure. Purification by flash column chromatography (SiO$_2$, EtOAc:Hex) afforded the pure product as a brown solid (0.40 gr, 78%).

1H NMR (CDCl$_3$, 400 MHz): δ 7.06 (d, J=8.6 Hz, 2H), 6.87 (d, J=8.7 Hz, 2H), 6.48 (d, J=12.3 Hz, 2H), 6.29 (d, J=7.6 Hz, 2H), 5.54 (s, 1H), 3.80 (s, 3H), 3.74 (q, J=7.2 Hz, 4H).

Example 8

Synthesis of 6,6'-((4-hydroxyphenyl)methylene)bis (4-fluoro-3-((2,2,2-trifluoroethyl)amino)phenol) (14)

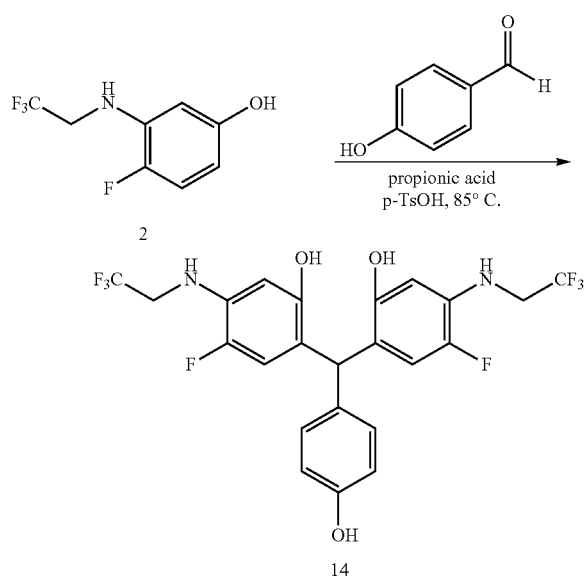

This process is based on B. R. Peterson et al. (*Beilstein J. Org. Chem.* 2012, 8, 2156-2165).

Compound 2 (2.0 gr, 9.5 mmol) was dissolved in propionic acid (40 ml). Then 4-hydroxybenzaldehyde (0.584 gr, 4.8 mmol) and catalytic p-TsOH were added at room temperature, and the reaction was heated to 80-85° C. for 5 h. After reaction completion, the solution was cooled to 0° C., poured into excess of aqueous sodium acetate solution (3 M, 300 ml) and extracted with ethyl acetate (450 ml). The organic layer was washed twice with water (300 ml), dried over MgSO$_4$ and concentrated under reduced pressure. Purification by flash column chromatography (SiO$_2$, EtOAc: Hex) afforded the pure product 14 as a brown-yellow solid (1.19 gr, 47%).

$^1$H NMR (CDCl$_3$, 400 MHz): δ 7.02 (d, J=8.4 Hz, 2H), 6.80 (d, J=8.6 Hz, 2H), 6.49 (d, J=12.3 Hz, 2H), 6.30 (d, J=7.5 Hz, 2H) 5.54 (s, 1H), 4.21-4.17 (m, 2H), 3.78-3.69 (m, 4H).

Example 9

Synthesis of Rosamine 8

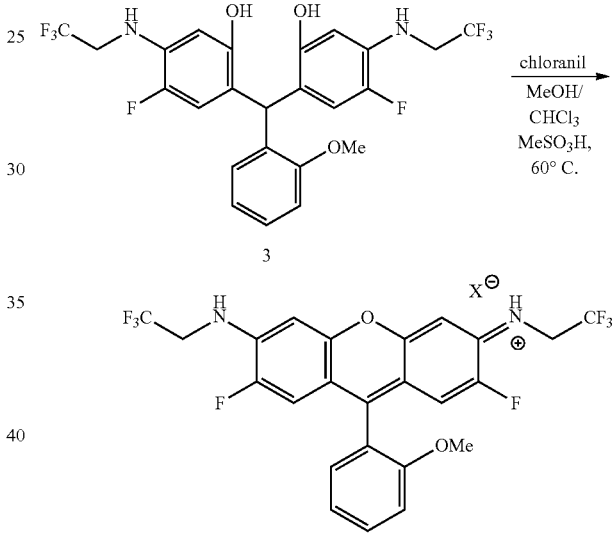

This process is based on B. R. Peterson et al. (*Beilstein J. Org. Chem.* 2012, 8, 2156-2165). To a stirred solution of 3 (0.34 gr, 0.64 mmol) and chloranil (0.24 gr, 0.96 mmol) in MeOH/CHCl$_3$ (1:1, 30 ml), MeSO$_3$H (2.0 ml) was added and the reaction mixture was heated at 60° C. for 2 hours. After reaction completion, solvents were evaporated, the crude was dissolved in EtOAc (50 ml) and washed with water (3×30 ml). The combined water fractions were extracted with THF (3×50 ml). The combined organic fractions were dried over MgSO$_4$ and concentrated under reduced pressure. Purification by flash column chromatography (SiO$_2$, Acetone:Methanol) afforded the pure product 8 as a brown solid.

$^1$H NMR (CDCl$_3$, 400 MHz): δ 7.55-7.51 (m, 1H), 7.14-7.08 (m, 3H), 6.60 (d, J=11.6 Hz, 2H), 6.53 (d, J=6.8 Hz, 2H), 3.96 (q, J=9.2 Hz, 4H), 3.73 (s, 3H).

UV-Vis absorption of Compound 8 is: 506 nm (in ethanol)

Fluorescence emission: 527 nm (in ethanol)

FWHM=32 nm

Example 10

Synthesis of Rosamine 9

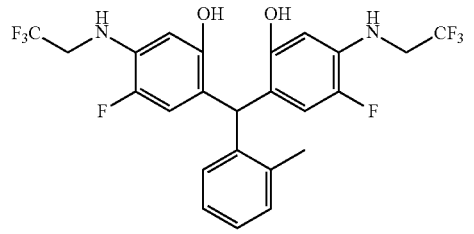

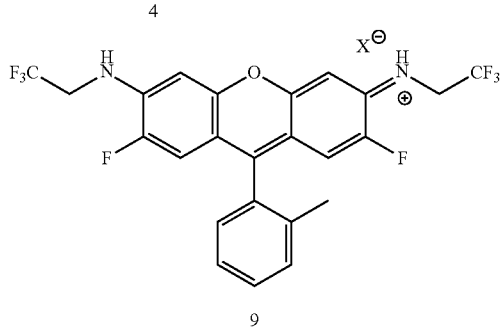

This process is based on B. R. Peterson et al. (*Beilstein J. Org. Chem.* 2012, 8, 2156-2165). To a stirred solution of 4 (0.35 gr, 0.67 mmol) and chloranil (0.25 gr, 1.00 mmol) in MeOH/CHCl$_3$ (1:1, 30 ml), MeSO$_3$H (2.0 ml) was added and the reaction mixture was heated at 60° C. for 2 hours. After reaction completion, solvents were evaporated, the crude was dissolved in EtOAc (50 ml) and washed with water (3×30 ml). The combined water fractions were extracted with THF (3×50 ml). The combined organic fractions were dried over MgSO$_4$ and concentrated under reduced pressure. Purification by flash column chromatography (SiO$_2$, Acetone:Methanol) afforded the pure product 9 as a brown solid.

$^1$H NMR (CDCl$_3$, 400 MHz): δ 7.45-7.34 (m, 3H), 7.10 (d, J=7.2 Hz, 1H), 6.57 (d, J=6.8 Hz, 2H), 6.53 (d, J=11.6 Hz, 2H), 5.12 (br s, 2H), 3.98 (q, J=8.8 Hz, 4H), 2.06 (s, 3H).
UV-Vis absorption of Compound 9 is: 505 nm (in ethanol)
Fluorescence emission: 525 nm (in ethanol)
FWHM=32 nm

Example 11

Synthesis of Rosamine 10

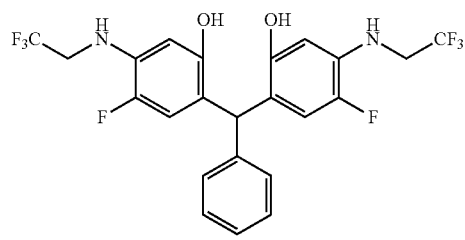

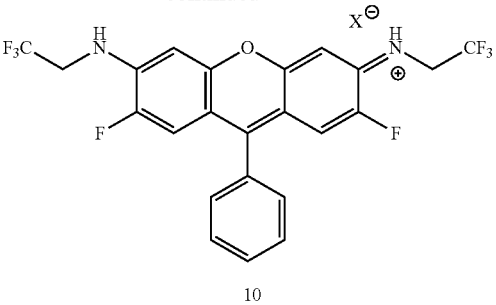

This process is based on B. R. Peterson et al. (*Beilstein J. Org. Chem.* 2012, 8, 2156-2165). To a stirred solution of 5 (0.26 gr, 0.52 mmol) and chloranil (0.19 gr, 0.78 mmol) in MeOH/CHCl$_3$ (1:1, 30 ml), MeSO$_3$H (2.0 ml) was added and the reaction mixture was heated at 60° C. for 2 hours. After reaction completion, solvents were evaporated, the crude was dissolved in EtOAc (50 ml) and washed with water (3×30 ml). The combined water fractions were extracted with THF (3×50 ml). The combined organic fractions were dried over MgSO$_4$ and concentrated under reduced pressure. Purification by flash column chromatography (SiO$_2$, Acetone:Methanol) afforded the pure product 10 as a brown solid.

$^1$H NMR (CDCl$_3$, 400 MHz): δ 7.37-7.34 (m, 2H), 7.28-7.25 (m, 2H), 7.20-7.16 (m, 1H), 6.74 (d, J=12.0 Hz, 2H), 6.50 (d, J=7.6 Hz, 2H), 4.38-4.34 (m, 2H), 3.86-3.77 (m, 4H), 2.90 (s, 3H).
UV-Vis absorption of Compound 10 is: 507 nm (in ethanol)
Fluorescence emission: 525 nm (in ethanol)
FWHM=35 nm

Example 12

Synthesis of Rosamine 11

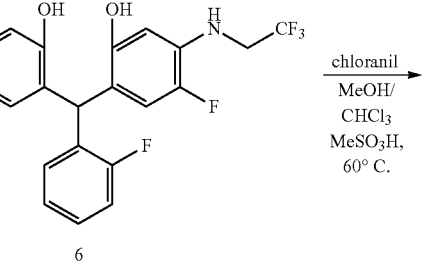

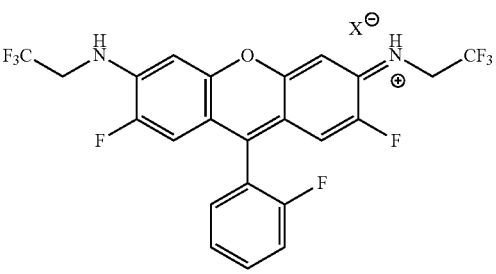

This process is based on B. R. Peterson et al. (*Beilstein J. Org. Chem.* 2012, 8, 2156-2165). To a stirred solution of 6

(0.15 gr, 0.29 mmol) and chloranil (0.11 gr, 0.43 mmol) in MeOH/CHCl₃ (1:1, 15 ml), MeSO₃H (0.5 ml) was added and the reaction mixture was heated at 60° C. for 2 hours. After reaction completion, solvents were evaporated, the crude was dissolved in EtOAc (25 ml) and washed with water (3×15 ml). The combined water fractions were extracted with THF (3×25 ml). The combined organic fractions were dried over MgSO₄ and concentrated under reduced pressure. Purification by flash column chromatography (SiO₂, Acetone:Methanol) afforded the pure product 11 as a brown solid.

¹H NMR (CDCl₃, 400 MHz): δ 8.09-8.05 (m, 1H), 7.25-7.21 (m, 2H), 6.83-6.21 (m, 1H), 6.69 (d, J=11.6 Hz, 2H), 6.50 (d, J=8.8 Hz, 2H), 4.36-4.33 (m, 2H), 3.85-3.76 (m, 4H), 2.84 (s, 3H).

UV-Vis absorption of Compound 11 is: 512 nm (in ethanol)

Fluorescence emission: 538 nm (in ethanol)

FWHM=41 nm

Example 13

Synthesis of Rosamine 12

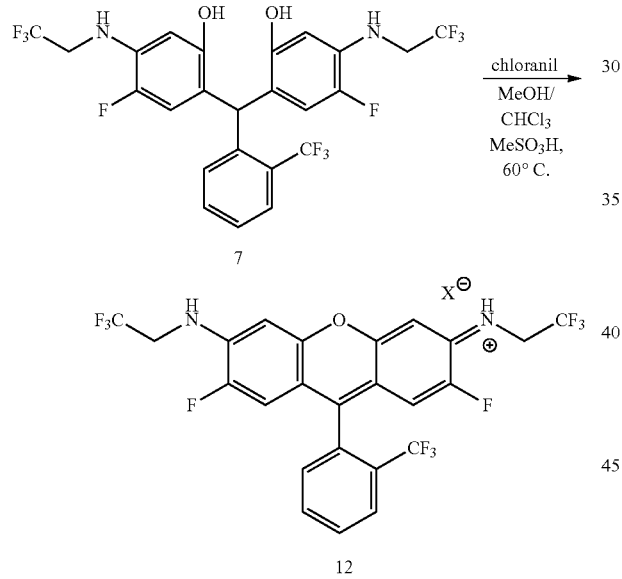

This process is based on B. R. Peterson et al. (*Beilstein J. Org. Chem.* 2012, 8, 2156-2165). To a stirred solution of 7 (0.33 gr, 0.57 mmol) and chloranil (0.21 gr, 0.85 mmol) in MeOH/CHCl₃ (1:1, 30 ml), MeSO₃H (1.0 ml) was added and the reaction mixture was heated at 60° C. for 2 hours. After reaction completion, solvents were evaporated, the crude was dissolved in EtOAc (50 ml) and washed with water (3×30 ml). The combined water fractions were extracted with THF (3×50 ml). The combined organic fractions were dried over MgSO₄ and concentrated under reduced pressure. Purification by flash column chromatogaphy (SiO₂, Acetone:Methanol) afforded the pure product 12 as a brown solid.

¹H NMR (CDCl₃, 400 MHz): δ 7.91 (d, J=7.2 Hz, 1H), 7.77-7.68 (m, 2H), 7.28 (d, J=7.6 Hz, 2H), 6.48 (d, J=6.4 Hz, 2H), 6.26 (d, J=11.6 Hz, 2H), 3.93 (q, J=8.8 Hz, 4H).

UV-Vis absorption of Compound 12 is: 514 nm (in ethanol)

Fluorescence emission: 533 nm (in ethanol)

FWHM=35 nm

Example 14

Synthesis of Rosamine 15

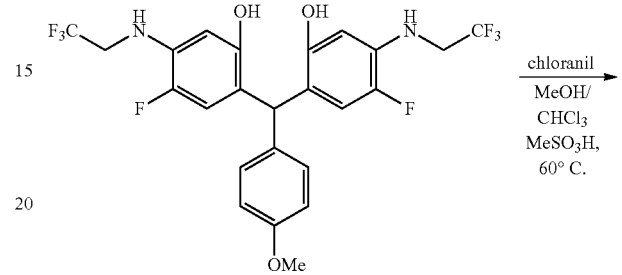

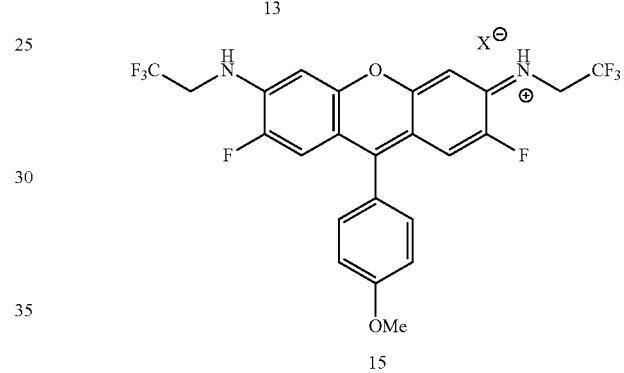

Synthesis of (Z)-N-(2,7-difluoro-9-(4-methoxyphenyl)-6-((2,2,2-trifluoroethyl)amino)-3H-xanthen-3-ylidene)-2,2,2-trifluoroethanaminium (15)

This process is based on B. R. Peterson et al. (*Beilstein J. Org. Chem.* 2012, 8, 2156-2165). To a stirred solution of 13 (0.40 gr, 0.74 mmol—see Example 7) and chloranil (0.27 gr, 1.1 mmol) in MeOH/CHCl₃ (1:1, 30 ml), MeSO₃H (2.0 ml) was added and the reaction mixture was heated at 60° C. for 2 hours. After reaction completion, solvents were evaporated, the crude was dissolved in EtOAc (50 ml) and washed with water (3×30 ml). The combined water fractions were extracted with THF (3×50 ml). The combined organic fractions were dried over MgSO₄ and concentrated under reduced pressure. Purification by flash column chromatogaphy (SiO₂, Acetone:Methanol) afforded the pure product 15 as a brown solid.

¹H NMR (MeOD-d4, 400 MHz): δ 7.53 (d, J=8.4 Hz, 2H), 7.48 (d, J=6.6 Hz, 2H), 7.41 (d, J=11.9 Hz, 2H), 5.30 (d, J=8.2 Hz, 2H), 4.35 (q, J=8.9 Hz, 4H), 3.98 (s, 3H).

UV-Vis absorption of Compound 15 is: 503 nm (in ethanol)

Fluorescence emission: 525 nm (in ethanol)

FWHM=35 nm

Example 15

Synthesis of Rosamine 16

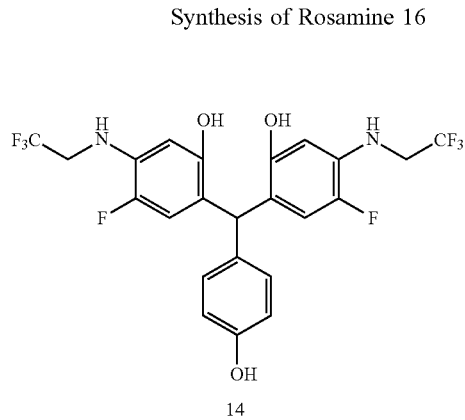

Synthesis of (Z)-N-(2,7-difluoro-9-(4-hydroxyphenyl)-6-((2,2,2-trifluoroethyl)amino)-3H-xanthen-3-ylidene)-2,2,2-trifluoroethanaminium (16)

This process is based on B. R. Peterson et al. (*Beilstein J. Org. Chem.* 2012, 8, 2156-2165). To a stirred solution of 14 (0.262 gr, 0.5 mmol-See Example 8) and chloranil (0.185 gr, 0.8 mmol) in MeOH/CHCl$_3$ (1:1, 15 ml), MeSO$_3$H (1.4 ml) was added and the reaction mixture was heated at 60° C. for 2 hours. After reaction completion, solvents were evaporated, the crude was dissolved in EtOAc (25 ml) and washed with water (3×15 ml). The combined water fractions were extracted with THF (3×25 ml). The combined organic fractions were dried over MgSO$_4$ and concentrated under reduced pressure. Purification by flash column chromatography (SiO$_2$, Dichloromethane:Methanol) afforded the pure product 16 as a brown solid.

$^1$H NMR (DMSO-d6, 400 MHz): δ 8.94-8.90 (m, 2H), 7.62 (d, J=7.1 Hz, 2H), 7.46-7.39 (m, 4H), 7.11 (d, J=8.6 Hz, 2H), 4.51-4.47 (m, 4H).

UV-Vis absorption of Compound 16 is: 501 nm (in ethanol)

Fluorescence emission: 523 nm (in ethanol)

FWHM=41 nm

What is claimed is:

1. A photoluminescent compound represented by the structure of formula (VII):

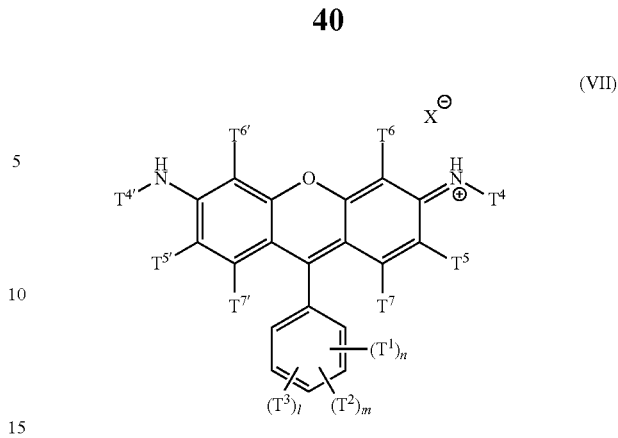

wherein $T^1$ each is independently H, $Q^1$, $OQ^1$, $CF_3$, $C(O)Q^1$, $NQ^1Q^2$, $NO_2$, CN, $SQ^1$, $-NQ^1Q^2CONQ^3Q^4$, NCO, NCS, $-OC(O)OQ^1$ or halide;

$T^2$ each is independently H, $Q^1$, $OQ^1$, $CF_3$, $C(O)Q^1$, $NQ^1Q^2$, $NO_2$, CN, $SQ^1$, $-NQ^1Q^2CONQ^3Q^4$, NCO, NCS, $-OC(O)OQ^1$ or halide;

$T^3$ each is independently H, $Q^1$, $OQ^1$, $CF_3$, $C(O)Q^1$, $NQ_1Q^2$, $NO_2$, CN, $SQ^1$, $-NQ^1Q^2CONQ^3Q^4$, NCO, NCS, $-OC(O)OQ^1$ or halide;

$T^4$ and $T^{4'}$ are each independently selected from alkyl, haloalkyl, heterocycloalkyl, cycloalkyl and benzyl;

$T^5$ and $T^{5'}$ are each independently selected from H, $-(CH_2)_pOC(O)NH(CH_2)_qSi(Oalkyl)_3$, $-(CH_2)_pOC(O)CH=CH_2$, $-(CH_2)_pSi(Oalkyl)_3$, $-OC(O)N(H)Q^4$, $-OC(S)N(H)Q^4$, $-N(H)C(O)N(Q^3)_2$, $-N(H)C(S)N(Q^3)_2$, $NQ^1Q^2CONQ^3Q^4$, NCO, NCS, alkenyl, alkynyl, epoxide, alkylated epoxide, azide and halide;

$T^6$, $T^{6'}$, $T^{7'}$ and $T^{7'}$ are each independently selected from H, $Q^1$, $OQ^1$, $CF_3$, $C(O)Q^1$, $COOQ^1$, $CON(Q^1)_2$, $NQ^1Q^2$, $NO_2$, CN, $SO_3^-$, $SO_3M$, $SO_3H$, $SQ^1$, $-NQ^1Q^2CONQ^3Q^4$, NCO, NCS, alkenyl, alkynyl, epoxide, alkylated epoxide, azide and halide; or $T^4$ and $T^5$ or $T^{4'}$ and $T^{5'}$ form together a N-heterocyclic ring wherein said ring is optionally substituted;

$Q^1$ and $Q^2$ are each independently selected from H, alkyl, haloalkyl, heterocycloalkyl, cycloalkyl, aryl, benzyl, $-(CH_2)_pOC(O)NH(CH_2)_qSi(Oalkyl)_3$, $-(CH_2)_pOC(O)CH=CH_2$, $-(CH_2)_pSi(Oalkyl)_3$, $-OC(O)N(H)Q^4$, $-OC(S)N(H)Q^4$, $-N(H)C(O)N(Q^3)_2$ and $-N(H)C(S)N(Q^3)_2$;

$Q^3$ and $Q^4$ are each independently selected from H, alkyl, haloalkyl, heterocycloalkyl, cycloalkyl, aryl and benzyl;

M is a monovalent cation;

n, m and l are independently an integer between 1-5;

p and q are independently an integer between 1-6;

$X^-$ is an anion;

wherein if one of $T^5$-$T^7$ and $T^{5'}$-$T^{7'}$ is $SO_3^-$, then X is omitted;

wherein if at least one of $T^4$ and $T^{4'}$ is haloalkyl—then at least one of $T^5$ and $T^{5'}$ is H or halide; and wherein if at least one of $T^4$ and $T^{4'}$ is alkyl—then all $T^1$-$T^3$ are each independently selected from H, $Q^1$, $OQ^1$, $CF_3$, $C(O)Q^1$, $NQ^1Q^2$, $NO_2$, CN, $SQ^1$, $-NQ^1Q^2CONQ^3Q^4$, NCO, NCS or $-OC(O)OQ^1$.

2. The photoluminescent compound of claim 1, wherein said compound is represented by the structure of formula (VIII):

(VIII)

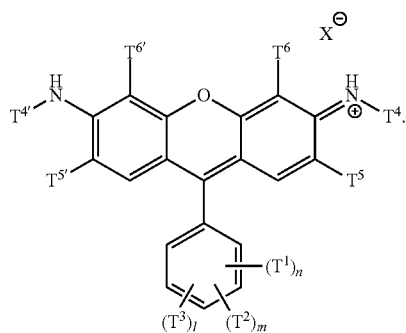

3. The photoluminescent compound of claim 2, wherein said compound is represented by the structure of formula (IX):

(IX)

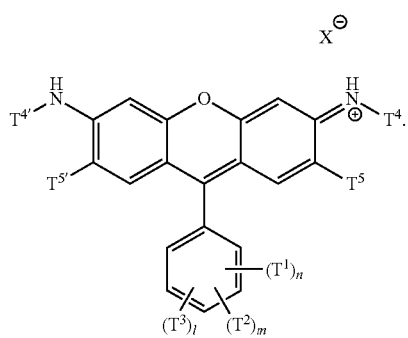

4. The photoluminescent compound of claim 3, wherein said compound is represented by the structure of formula (X):

(X)

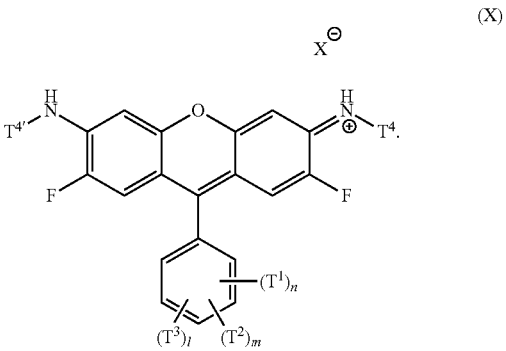

5. The photoluminescent compound of claim 1, wherein said anion is a sulfate, chloride, bromide, iodide, perchlorate, nitrate, trifluoroacetate, hydroxide, hydrosulfide, sulfide, nitrite, carboxylate, dicarboxylate, sulfonate, tetrafluoroborate, hexafluorophosphate, hypophosphite, phosphate, phosphite, cyanate, cyanide, isocyanate, thiocyanate, tetraalkylborate, tetra-arylborate or chromate.

6. A photoluminescent device comprising a color-conversion layer comprising a photoluminescent compound according to claim 1.

7. The photoluminescent device of claim 6, wherein said color-conversion-layer is in a form of a film.

8. The photoluminescent device of claim 7, wherein said photoluminescent compound comprises an emission peak between 520-560 nm and FWHM between 30 and 55 nm.

* * * * *